United States Patent
Gutmann et al.

(10) Patent No.: US 11,085,933 B2
(45) Date of Patent: Aug. 10, 2021

(54) NEUROFIBROMIN/DOPAMINE SIGNALING AS A BIOMARKER FOR COGNITIVE AND BEHAVIORAL PROBLEMS IN CHILDREN WITH NEUROFIBROMATOSIS TYPE 1 (NF1)

(71) Applicant: Washington University in St. Louis, St. Louis, MO (US)

(72) Inventors: David H. Gutmann, St. Louis, MO (US); Corina Anastasaki, St. Louis, MO (US)

(73) Assignee: Washington University in St. Louis, St. Louis, MO (US)

( * ) Notice: Subject to any disclaimer, the term of this patent is extended or adjusted under 35 U.S.C. 154(b) by 0 days.

(21) Appl. No.: 16/593,316

(22) Filed: Oct. 4, 2019

(65) Prior Publication Data

US 2020/0041527 A1 Feb. 6, 2020

Related U.S. Application Data

(63) Continuation of application No. 15/187,298, filed on Jun. 20, 2016, now abandoned.

(51) Int. Cl.
| | | |
|---|---|---|
| *G01N 33/53* | (2006.01) | |
| *G01N 33/68* | (2006.01) | |
| *C12Q 1/6883* | (2018.01) | |

(52) U.S. Cl.
CPC ....... *G01N 33/6893* (2013.01); *C12Q 1/6883* (2013.01); *C12Q 2600/156* (2013.01); *C12Q 2600/158* (2013.01); *G01N 2333/4704* (2013.01); *G01N 2440/14* (2013.01); *G01N 2800/30* (2013.01)

(58) Field of Classification Search
None
See application file for complete search history.

(56) References Cited

U.S. PATENT DOCUMENTS

| | | |
|---|---|---|
| 6,365,126 B1 | 4/2002 | Zhong et al. |
| 7,320,785 B2 | 1/2008 | Greengard et al. |
| 8,101,606 B2 | 1/2012 | Gutmann et al. |
| 8,222,293 B2 | 7/2012 | Silva et al. |
| 2007/0004767 A1 | 1/2007 | Gutmann et al. |

OTHER PUBLICATIONS

GenBank reference sequence Accession No. NM_00104292.2.
GenBank reference sequence Accession No. NM_010897.2, Oct. 2015.
Apr. 2016 GenBank reference sequence Accession No. NM_000267.3, Apr. 2016.
GenBank reference sequence Accession No. NP_000258.1, Apr. 2016.
Anastasaki, et al., Elucidating the impact of neurofibromatosis-1 germline mutations on neurofibromin function and dopamine-based learning, Human Molecular Genetics, 2015, pp. 1-11.
Digs-Andrews, et al., Sex is a major determinant of neuronal dysfunction in Neurofibromatosis Type 1, 2015, Ann Neurol., pp. 1-13.
Karlsgodt et al., Alterations in White Matter Microstructure in Neurofibromatosis-1; PLOS one; 11-pages.

*Primary Examiner* — James Martinell
(74) *Attorney, Agent, or Firm* — Stinson LLP

(57) ABSTRACT

The present disclosure is generally related to neurofibromatosis type 1. More particularly, disclosed herein are methods for detecting behavioral disorders, methods for detecting cognitive impairment, and methods for detecting brain neurofibromin-dependent dopaminergic signaling associated with neurofibromatosis type 1.

19 Claims, 15 Drawing Sheets
(5 of 15 Drawing Sheet(s) Filed in Color)
Specification includes a Sequence Listing.

FIG. 2A
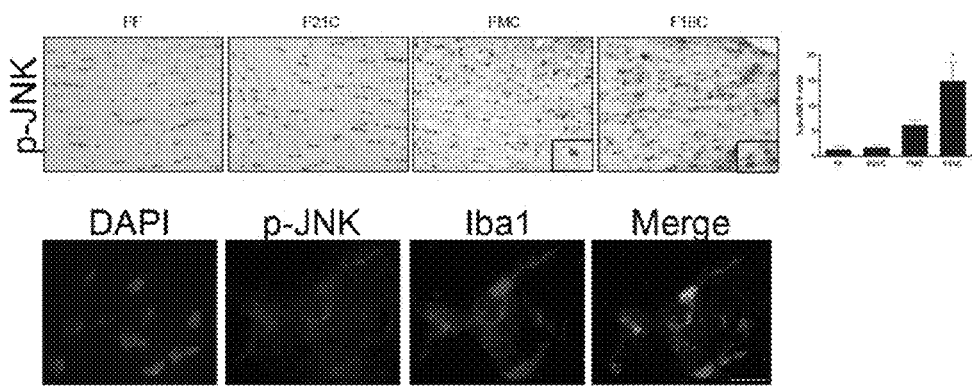
FIG. 2B
FIG. 2C
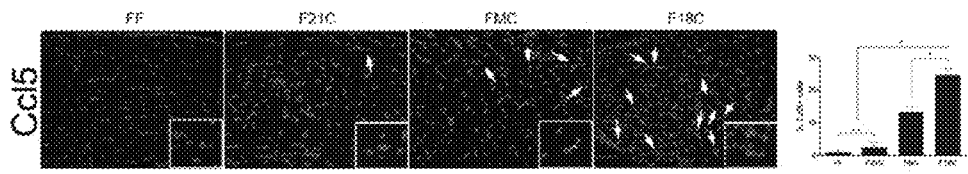
FIG. 2D
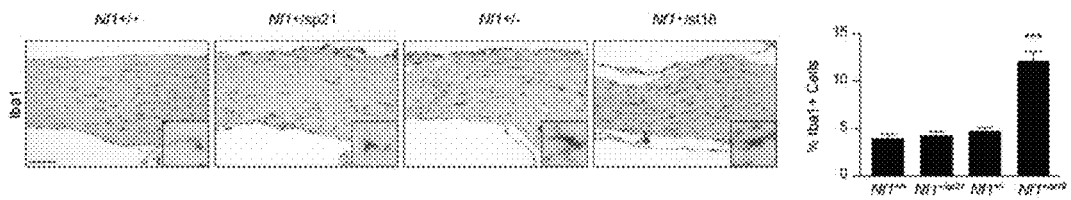

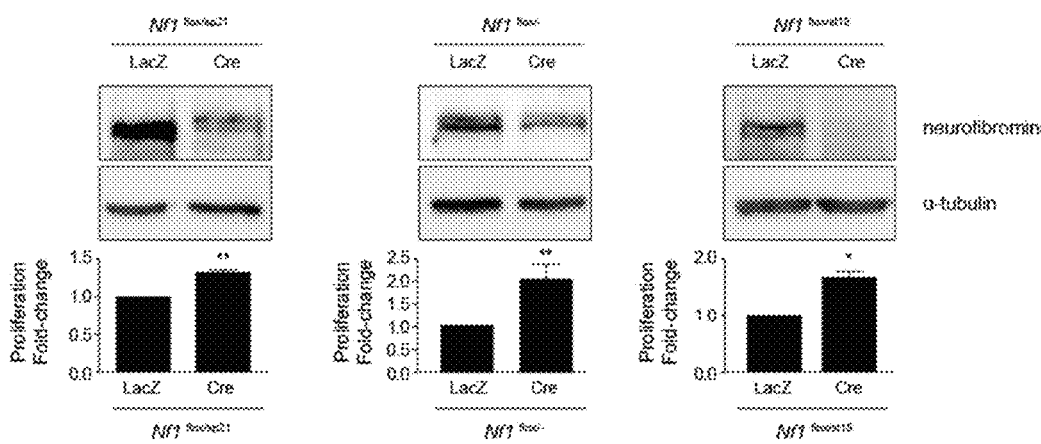

NEUROFIBROMIN/DOPAMINE SIGNALING AS A BIOMARKER FOR COGNITIVE AND BEHAVIORAL PROBLEMS IN CHILDREN WITH NEUROFIBROMATOSIS TYPE 1 (NF1)

CROSS-REFERENCE TO RELATED APPLICATIONS

This application is a continuation application of U.S. Patent Publication No. 2016/0370383, filed on Jun. 20, 2016 (abandoned), which claims priority under 35 U.S.C § 119(e) to U.S. Provisional Application No. 62/181,949, filed on Jun. 19, 2015, each of which is hereby incorporated by reference in its entirety.

STATEMENT REGARDING FEDERALLY SPONSORED RESEARCH OR DEVELOPMENT

This invention was made with government support under 5-T32-EY013360, NS007205, and CA195692 awarded by The National Institutes of Health. The Government has certain rights in the invention.

INCORPORATION OF SEQUENCE LISTING

A paper copy of the Sequence Listing and a computer readable form of the Sequence Listing containing the file named "WUSTL015422_5 T25.txt", which is 82,262 bytes in size (as measured in MICROSOFT WINDOWS® EXPLORER), are provided herein and are herein incorporated by reference. This Sequence Listing consists of SEQ ID NO:1-4.

BACKGROUND OF THE DISCLOSURE

The present disclosure relates generally to neurofibromatosis type 1. More particularly, the present disclosure is directed to methods for detecting behavioral disorders, methods for detecting cognitive impairment, and methods for detecting neurofibromin-dependent dopaminergic signaling associated with neurofibromatosis type 1.

Neurofibromatosis type 1 (NF1) is a monogenic neurodevelopmental disorder affecting ~1 in 2500 individuals worldwide. Greater than 50% of individuals with NF1 exhibit cognitive deficits, which affect scholastic abilities and impact quality of life. These cognitive impairments include specific learning disabilities, attention deficits, autistic-like behaviors and visuospatial learning/memory problems. The specific cognitive symptoms as well as their severity vary greatly among individuals with NF1. Some children with NF1 can have problems with reading or mathematic achievement, while others exhibit deficits in visual perception or response inhibition. There may be cellular and molecular etiologies for these cognitive delays, which may explain why a small number of children respond to targeted therapeutic interventions.

Neurofibromin functions as a negative regulator of RAS and a positive regulator of dopamine homeostasis. High levels of RAS activation and low levels of dopamine have been reported in the brains of Nf1 genetically-engineered mice. Treatments such as lovastin (a RAS inactivator) or dopamine uptake blockers can ameliorate the spatial learning and memory deficits in mice.

A challenge to the management of children with NF1 is the lack of predictive markers to identify individuals with a risk for specific morbidities. Evidence from early-phase NF1 gene mutation studies has suggested that some types of germline NF1 gene mutations may be associated with certain clinical features. Cognitive problems in neurological disorders can be difficult to identify, especially in non-verbal or young children. Accordingly, there exists a need to identify predictive markers for disease phenotypes in NF1 patients.

BRIEF DESCRIPTION OF THE DISCLOSURE

The present disclosure is generally related to neurofibromatosis type 1. More particularly, the present disclosure is directed to methods for detecting behavioral disorders, methods for detecting cognitive impairment, and methods for detecting neurofibromin-dependent dopaminergic signaling associated with neurofibromatosis type 1.

In one aspect, the present disclosure is directed to a method for detecting a behavioral disorder in a subject having or suspected of having neurofibromatosis type 1 (NF1). The method comprises obtaining an expression level of neurofibromin in a sample obtained from the subject having or suspected of having neurofibromatosis type 1 (NF1); obtaining a reference expression level of neurofibromin from a healthy subject; identifying a difference between the expression level of the neurofibromin in the sample obtained from the subject and the reference expression level of the neurofibromin, wherein the difference between the expression level of the neurofibromin in the sample obtained from the subject and the reference expression level of the neurofibromin indicates a memory defect in a subject having or suspected of having neurofibromatosis type 1 (NF1).

In another aspect, the present disclosure is directed to a method for detecting a cognitive impairment in a subject having or suspected of having neurofibromatosis type 1 (NF1). The method comprises: obtaining an expression level of neurofibromin in a sample obtained from the subject having or suspected of having neurofibromatosis type 1 (NF1); obtaining a reference expression level of neurofibromin from a healthy subject; identifying a difference between the expression level of the neurofibromin in the sample obtained from the subject and the reference expression level of the neurofibromin, wherein the difference between the expression level of the neurofibromin in the sample obtained from the subject and the reference expression level of the neurofibromin indicates a cognitive impairment in a subject having or suspected of having neurofibromatosis type 1 (NF1).

In another aspect, the present disclosure is directed to a method for detecting altered brain neurofibromin-dependent dopaminergic signaling in a subject having or suspected of having neurofibromatosis type 1 (NF1). The method comprises: obtaining an expression level of neurofibromin in a sample obtained from the subject having or suspected of having neurofibromatosis type 1 (NF1); obtaining a reference expression level of neurofibromin from a healthy subject; identifying a difference between the expression level of the neurofibromin in the sample obtained from the subject and the reference expression level of the neurofibromin, wherein the difference between the expression level of the neurofibromin in the sample obtained from the subject and the reference expression level of the neurofibromin indicates a memory defect in a subject having or suspected of having neurofibromatosis type 1 (NF1).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIG. 1A is a schematic illustration of the mouse Nf1 gene and summary of the engineered Nf1 mouse germline mutations with genotyping results. Alternate exons and the RAS-GAP domain are indicated. The position of the three introduced germline mutations is depicted above exons 18, 21 and 31. FIG. 1B (top panel) are photographs showing increased optic nerve volumes in FMC and F18C optic nerves compared to controls while no significant changes were detected between F21C and controls; (bottom panel) Hematoxylin and eosin staining of optic nerves reveal hypercellularity, increased mitotic figures and nuclear atypia in FMC and F18C with a significant increase in cell number in F18C mice. FIG. 1C depicts increased GFAP (top) and Ki67 (bottom) immunoreactivity in F18C mice compared to FMC mice. FIG. 1D depicts immunostaining with Iba1 demonstrating a significantly increased number of microglia in the optic nerve of FMC and F18C mice compared to controls. No significant difference was shown in microglia number between F21C and WT controls. Furthermore, F18C mice had significantly more microglia than FMC mice. FIG. 1E depicts an increase in the percentage of TUNEL$^+$ cells (top panel), lower percentage of Brn3a$^+$ cells (middle panel) and thinning of RNFL (SMI-32 immunostaining) in F18C mice as compared to FMC mice as well as F21C and controls. Scale bar, 100 µm. All data are represented as means±s.e.m.

FIG. 2A-2D depict the regulation of microglial activation and infiltration by Nf1 germline mutation. FIG. 2A (top panel) depicts increased pJNK immunoreactivity in FMC and F18C optic nerves compared to FF controls and F21C optic nerves; (bottom panel) depicts immunofluorescent staining revealing pJNK staining in Iba1 positive cells. FIG. 2B depicts increased CCL5 immunostaining in FMC and F18C optic nerves. FIG. 2C depicts elevation of pAkt.308 only in F18C optic nerves compared to F21C, FMC optic nerves and FF controls. FIG. 2D depicts immunostaining with Iba1 revealing significantly increased number of microglia in Nf1$^{+/st18}$ optic nerves compared to WT (Nf1$^{+/+}$), Nf1$^{+/sp21}$ and Nf1$^{+/-}$ mice. Scale bar 100 µm. Data are represented as means±s.e.m. (***P<0.0001; One-way ANOVA with Bonferroni post-test).

FIG. 3A depicts immunoblot analysis of neurofibromin in hippocampi of wild-type (Nf1$^{+/+}$; WT) and heterozygous mutant Nf1 mice: Nf1$^{+/sp21}$, Nf1$^{+/-}$ and Nf1$^{+/st18}$ Neurofibromin expression was significantly reduced by 39%, 50% and 76% in Nf1$^{+/sp21}$, Nf1$^{+/-}$ and Nf1$^{+/st18}$ mice, respectively, compared to controls. α-tubulin was used as an internal loading control. FIG. 3B depicts elevation of RAS activity (RAS-GTP) in Nf1$^{+/sp21}$, Nf1$^{+/-}$ and Nf1$^{+/st18}$ hippocampi compared to controls. Total RAS was used as a loading control. FIG. 3C depicts reduction in cAMP levels in Nf1$^{sp21/+}$, Nf1$^{+/-}$ and Nf1$^{+/st18}$ hippocampi compared to WT controls.

FIG. 4A depicts the decrease in dopamine levels in all Nf1 mutant mice. Dopamine was reduced by 38%, 50% and 64% in Nf1$^{+/sp21}$, Nf1$^{+/-}$ and Nf1$^{+/st18}$ hippocampi, respectively, compared to WT controls. FIG. 4B depicts the decrease in DARPP-32 activity (phosphorylation) by 44% in Nf1$^{+/sp21}$, 51% in Nf1$^{+/-}$ and 77% in Nf1$^{+/st18}$ hippocampi, compared to controls. FIGS. 4C & 4D. Left panel: All mice preferentially occupied the target (Tgt) quadrant of the water maze. The dashed line represents chance occupancy of any quadrant. Right panel: Nf1$^{+/st18}$ mice spent significantly less time in the target quadrant compared to their WT littermate controls (Nf1$^{+/+}$). Nf1$^{+/sp21}$ mice showed no memory deficit in the Morris water maze. (FIGS. 4A-4B: ***P<0.0001; *P<0.01; One-way ANOVA with Bonferroni post-test. FIG. 4C: ***P<0.0001; Two-way ANOVA with Bonferroni post-test; *P<0.01; Student's t-test).

FIG. 5A depicts a Neurofibromin immunoblot revealing a reduction in neurofibromin expression in white blood cells (WBC) of Nf1$^{+/sp21}$ (40%), Nf1$^{+/-}$ (50%) and Nf1$^{+/st18}$ (70%) mice compared to WT controls (Nf1$^{+/+}$). FIG. 5B depicts the correlation of relative neurofibromin expression detected in hippocampi and WBC (R2=0.9700). FIG. 5C depicts the decrease of dopamine (DA) levels in Nf1$^{+/sp21}$ (40%), Nf1$^{+/-}$ (50%) and Nf1$^{+/st18}$ (60%) WBC compared to WT controls. FIG. 5D depicts the correlation of relative neurofibromin expression and DA levels in WBC samples (R2=0.9881). FIG. 5E depicts the correlation of relative DA levels detected in hippocampi and WBC (R2=0.9015). FIG. 5F depicts the decrease of DARPP-32 phosphorylation in Nf1$^{+/sp21}$ (40%), Nf1$^{+/-}$ (50%) and Nf1$^{+/st18}$ (70%) WBC compared to wild-type controls. FIG. 5G depicts the correlation of relative neurofibromin expression and DARPP-32 phosphorylation in WBC (R2=0.9891). FIG. 5H depicts the correlation of relative DARPP-32 phosphorylation detected in hippocampi and WBC (R2=0.9162). Data are represented as means±s.e.m. (***P<0.0001; One-way ANOVA with Bonferroni post-test).

FIGS. 6A & 6B depict the effect of all germline Nf1 mutations on astrocyte proliferation. FIG. 6A depicts immunoblot analysis of neurofibromin FIG. 6B are graphs depicting fold change in proliferation. Astrocyte proliferation was increased upon Nf1 gene inactivation (Cre) in all germline mutation bearing astrocytes compared to heterozygous control astrocytes (LacZ). Data are represented as means±s.e.m. (**P<0.001; *P<0.005; Student's t-test).

FIG. 7A depicts immunostaining with pAkt$^{Ser473}$ (images in left panel) and percent p-AKT$^{Ser473+}$ cells (graph in right panel) revealing significantly higher immunoreactivity in optic nerves of FMC and F18C animals relative to F21C and FF controls. FIG. 7B depicts immunostaining with p-S6$^{Ser240-244}$ (images in left panel) and percent p-S6$^{Ser240-244+}$ cells (graph in right panel) revealing significantly higher immunoreactivity in optic nerves of FMC and F18C animals relative to F21C and FF controls. Data are represented as means±s.e.m. (**P<0.001; *P<0.0.01; One-way ANOVA with Bonferroni post-test).

FIG. 10A depicts immunoblot of neurofibromin in hippocampi of wild-type (FF), heterozygous null Nf1$^{GFAP}$ flox/sp21, (F21C) and Nf1$^{GFAP}$ flox/st18 (F18C) and null Nf1$^{GFAP}$ flox/– (FMC) mice normalized to α-tubulin. Neurofibromin expression was significantly reduced in F21C, FMC and F18C mice hippocampi, compared to controls. FIG. 10B depicts elevation of RAS-GTP levels in F21C, FMC and F18C hippocampi, compared to WT controls. There was no significant difference between F21C, FMC and F18C hippocampi. FIG. 10C depicts reduced cAMP levels in F21C, FMC and F18C hippocampi compared to WT controls. There was no significant difference between F21C, FMC and F18C hippocampi. FIG. 10D (left panel) depicts the occupation of the target quadrant of the water maze compared to quadrants opposite (Opp) from, to the left of, and to the right of the target quadrant. All mice preferentially occupied the target (Tgt) quadrant of the water maze compared to the quadrants opposite (Opp), left and right to it. The dashed line represents chance occupancy of any quadrant (15 sec). FIG. 10D (right panel) depicts the time mice spent in the target quadrant. F18C mice spent significantly less time in the target quadrant compared to F21C and FF controls. The dashed line represents time spent in the target quadrant by FMC mice. FIG. 10E depicts the reduction in dopamine levels in F21C, FMC and F18C hippocampi compared to controls. FIG. 10F depicts the decrease in DARPP-32 phosphorylation in F21C, FMC and F18C hippocampi compared to controls. All data are represented as means±s.e.m. (*P<0.0001; P<0.001; One-way/two-way ANOVA with Bonferroni post-test).

FIG. 12A is a neurofibromin immunoblot of NF1-patient fibroblasts demonstrating two groups showing reductions of neurofibromin expression. Group 1 patients have a <25% reduction in neurofibromin expression (n=4) and Group 2 patients have a >70% reduction in neurofibromin expression (n=7) when analyzed versus sex- and age-matched control individuals. Tubulin was used as an internal protein loading control. FIG. 12B depicts elevation of RAS activity in all NF1-patient fibroblasts. FIG. 12C is a schematic representation of the NF1 gene with the identified NF1-patent mutations and summary of NF1-patient germline NF1 gene mutations, demographic information and genotyping results. The number of exon mutated is indicated above the mutation location. Light and dark boxes indicate alternate exons. Horizontal bars represent the length of the predicted transcribed mRNA. TGD, total genomic deletion; FS, frame shift mutation. All data are represented as means±SEM (*P<0.0001, one-way ANOVA with Bonferroni post-test).

FIG. 13A depicts immunostaining of iPSC cultures with stem cell-specific antibodies confirming the pluripotent nature of the cultured iPSCs. Scale bar, 50 µm. FIG. 13B depicts bright-field images of representative iPSCs. Scale bar, 100 µm. FIG. 13C depicts the reduction of neurofibromin expression in Group 2 NF1-patient-derived iPSCs. FIG. 13D depicts the elevated RAS activity levels (RAS-GTP) in all NF1-patient-derived iPSCs relative to control iPSC lines. All data are represented as means±SEM (*P<0.0001, one-way ANOVA with Bonferroni post-test).

FIG. 14A are bright-field images and immunostaining of NPC cultures with the SMI-312 pan-axonal (neuronal) antibody. Scale bar left panel, 100 µm. Scale bar right panel, 50 µm. FIG. 14B depicts that neurofibromin expression was only significantly different in Group 2 NF1-patient samples relative to control NPCs. FIG. 14C depicts the elevated RAS activity levels in all NF1-patient NPCs. FIG. 14D depicts the decreased cAMP levels in all NF1-patient NPCs relative to control NPCs.

FIG. 15A depicts the reduction of dopamine (DA) levels in Group 2 NF1-patient samples relative to control NPCs. FIG. 15B depicts the relationship between neurofibromin expression and DA levels. FIG. 15C depicts the reduction of DARPP-32 activity (phosphorylation) only in Group 2 NF1-patient samples relative to control NPCs. FIG. 15D depicts the relationship between neurofibromin expression and DARPP-32 phosphorylation. All data are represented as means±SEM (*P<0.0001, one-way ANOVA with Bonferroni post-test).

DETAILED DESCRIPTION

Figure 1A:
FIGS. 1A-1E depict the influence of Nf1 germline mutations on tumor formation.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Disclosed are methods for detecting behavioral disorders, methods for detecting memory defects, and methods for detecting hippocampal neurofibromin-dependent dopaminergic signaling associated with neurofibromatosis type 1.

As used herein, "a subject in need thereof" refers to a subject having, susceptible to or at risk of a specified disease, disorder, or condition. More particularly, in the present disclosure the methods of screening biomarkers is to be used with a subset of subjects who have, are susceptible to or are at an elevated risk for experiencing behavioral disorders, memory defects, and/or altered brain neurofibromin-dependent dopaminergic signaling associated with neurofibromatosis type 1. Such subjects can be susceptible to or at elevated risk for behavioral disorders, memory defects, and/or altered brain neurofibromin-dependent dopaminergic signaling due to family history, age, environment, and/or lifestyle.

Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

As used herein, "susceptible" and "at risk" refer to having little resistance to a certain disease, disorder or condition, including being genetically predisposed, having a family history of, and/or having symptoms of the disease, disorder or condition.

As used herein, "expression level of a biomarker" refers to the process by which a gene product is synthesized from a gene encoding the biomarker as known by those skilled in the art. The gene product can be, for example, RNA (ribonucleic acid) and protein. Expression level can be quantitatively measured by methods known by those skilled in the art such as, for example, northern blotting, amplification, polymerase chain reaction, microarray analysis, tag-based technologies (e.g., serial analysis of gene expression and next generation sequencing such as whole transcriptome shotgun sequencing or RNA-Seq), Western blotting, enzyme linked immunosorbent assay (ELISA), and combinations thereof.

As used herein, "a reference expression level of a biomarker" refers to the expression level of a biomarker established for a subject without neurofibromatosis type 1, expression level of a biomarker in a normal/healthy subject without neurofibromatosis type 1 as determined by one skilled in the art using established methods as described herein, and/or a known expression level of a biomarker obtained from literature. The reference expression level of the biomarker can also refer to the expression level of the biomarker established for any combination of subjects such as a subject without neurofibromatosis type 1, expression level of the biomarker in a normal/healthy subject without neurofibromatosis type 1, and expression level of the biomarker for a subject without neurofibromatosis type 1 at the time the sample is obtained from the subject, but who later exhibits without neurofibromatosis type 1. The reference expression level of the biomarker can also refer to the expression level of the biomarker obtained from the subject to which the method is applied. As such, the change within a subject from visit to visit can indicate an increased or decreased risk for neurofibromatosis type 1. For example, a plurality of expression levels of a biomarker can be obtained from a plurality of samples obtained from the same subject and used to identify differences between the pluralities of expression levels in each sample. Thus, in some embodiments, two or more samples obtained from the same subject can provide an expression level(s) of a blood biomarker and a reference expression level(s) of the blood biomarker.

In one aspect, the present disclosure is directed to a method for detecting a behavioral disorder in a subject having or suspected of having neurofibromatosis type 1 (NF1). The method includes: obtaining an expression level of neurofibromin in a sample obtained from the subject having or suspected of having neurofibromatosis type 1 (NF1); obtaining a reference expression level of neurofibromin from a healthy subject; identifying a difference between the expression level of the neurofibromin in the sample obtained from the subject and the reference expression level of the neurofibromin, wherein the difference between the expression level of the neurofibromin in the sample obtained from the subject and the reference expression level of the neurofibromin indicates a behavioral disorder in a subject having or suspected of having neurofibromatosis type 1 (NF1).

Suitably, the expression level of the neurofibromin in the sample obtained from the subject is reduced when analyzed against the reference expression level. In an embodiment where the expression level of neurofibromin is obtained from a hippocampal sample as detected by Western blot analysis, the expression level of neurofibromin can be reduced by greater than 70% versus a reference expression level of neurofibromin obtained from a hippocampal sample obtained from a healthy subject. In another embodiment where the expression level of neurofibromin is obtained from white blood cells from a blood sample as detected by Western blot analysis, the expression level of neurofibromin can be reduced by greater than 70% versus a reference expression level of neurofibromin obtained from white blood cells from a blood sample obtained from a healthy subject.

The method can further include identifying an expression level of dopamine Suitably, the expression level of the dopamine in the sample obtained from the subject is reduced when analyzed against the reference expression level. In an embodiment where the expression level of dopamine is obtained from a hippocampal sample as detected by Western blot analysis, the expression level of dopamine can be reduced by greater than 70% versus a reference expression level of dopamine obtained from a hippocampal sample obtained from a healthy subject. In an embodiment where the expression level of dopamine is obtained from white blood cells from a blood sample as detected by Western blot analysis, the expression level of dopamine can be reduced by greater than 70% versus a reference expression level of dopamine obtained from white blood cells from a blood sample obtained from a healthy subject.

The method can further include identifying phosphorylation of dopamine and cAMP regulated neuronal phosphoprotein (DARPPP-32). Suitably, the phosphorylation the DARPPP-32 in the sample obtained from the subject is reduced when analyzed against phosphorylation of DARPPP-32 obtained from a hippocampal sample obtained from a healthy subject. In an embodiment where the expression level of neurofibromin is obtained from a hippocampal sample as detected by Western blot analysis, the expression level of DARPPP-32 can be reduced by greater than 70% versus a reference expression level of DARPPP-32 obtained from a hippocampal sample obtained from a healthy subject. In an embodiment where the phosphorylation of DARPPP-32 is obtained from white blood cells from a blood sample as detected by Western blot analysis, the phosphorylation of DARPPP-32 can be reduced by greater than 70% versus a phosphorylation of DARPPP-32 obtained from white blood cells from a blood sample obtained from a healthy subject.

In another embodiment, the method can further include detecting a point mutation in an exon of the Nf1 gene. The Nf1 gene can be a human Nf1 gene (see, Accession No. NM_00104292.2) and a mouse Nf1 gene (see, Accession No. NM_010897.2). Suitable exons in which a point mutation can be detected can be exon 18, exon 21, and combinations thereof. A particularly suitable point mutation to be detected in exon 18 is c.2041C>T of the human Nf1 gene (see, Accession No. NM_00104292.2). A particularly suitable point mutation to be detected in exon 21 is c.2542G>C of the human Nf1 gene (see, Accession No. NM_00104292.2).

Suitable samples can be brain, hippocampi, peripheral white blood cells, skin, and combinations thereof.

Suitable subjects can be any vertebrate species. Particularly suitable subjects can be humans and rodents. Suitable humans can be children. Particularly suitable human children include children having or suspected of having neurofibromatosis type 1 (NF1). Particularly suitable rodents include mice.

In another aspect, the present disclosure is directed to a method for detecting a cognitive impairment in a subject having or suspected of having neurofibromatosis type 1 (NF1). The method includes: obtaining an expression level of neurofibromin in a sample obtained from the subject having or suspected of having neurofibromatosis type 1 (NF1); obtaining a reference expression level of neurofibromin from a healthy subject; identifying a difference between the expression level of the neurofibromin in the sample obtained from the subject and the reference expression level of the neurofibromin, wherein the difference between the expression level of the neurofibromin in the sample obtained from the subject and the reference expression level of the neurofibromin indicates a cognitive impairment in a subject having or suspected of having neurofibromatosis type 1 (NF1).

Suitably, the expression level of the neurofibromin in the sample obtained from the subject is reduced when analyzed against the reference expression level as described herein.

The method can further include identifying an expression level of dopamine Suitably, the expression level of the dopamine in the sample obtained from the subject is reduced when analyzed against the reference expression level as described herein.

The method can further include identifying phosphorylation of dopamine and cAMP regulated neuronal phosphoprotein (DARPPP-32). Suitably, the phosphorylation of DARPPP-32 in the sample obtained from the subject is reduced when analyzed against the reference expression level as described herein.

The method can further include detecting a point mutation in an exon of the Nf1 gene. The Nf1 gene can be a human Nf1 gene (see, Accession No. NM_00104292.2) and a mouse Nf1 gene (see, Accession No. NM_010897.2). Suitable exons in which a point mutation can be detected can be exon 18, exon 21, and combinations thereof. A particularly suitable point mutation to be detected in exon 18 is c.2041C>T of the human Nf1 gene (see, Accession No. NM_00104292.2). A particularly suitable point mutation to be detected in exon 21 is c.2542G>C of the human Nf1 gene (see, Accession No. NM_00104292.2).

Suitable samples can be brain, hippocampi, peripheral white blood cells, skin, and combinations thereof.

Suitable subjects can be any vertebrate species. Particularly suitable subjects can be humans and rodents as described herein. Particularly suitable human children include children having or suspected of having neurofibromatosis type 1 (NF1).

Cognitive impairments can be selected from learning disabilities, attention deficits, autistic-like behaviors, visuospatial learning/memory problems and combinations thereof.

In another aspect, the present disclosure is directed to a method for detecting brain neurofibromin-dependent dopaminergic signaling in a subject having or suspected of having neurofibromatosis type 1 (NF1). The method includes: obtaining an expression level of neurofibromin in a sample obtained from the subject having or suspected of having neurofibromatosis type 1 (NF1); obtaining a reference expression level of neurofibromin from a healthy subject; identifying a difference between the expression level of the neurofibromin in the sample obtained from the subject and the reference expression level of the neurofibromin, wherein the difference between the expression level of the neurofibromin in the sample obtained from the subject and the reference expression level of the neurofibromin indicates a memory defect in a subject having or suspected of having neurofibromatosis type 1 (NF1).

In one embodiment, the present disclosure is directed to a method for detecting hippocampal neurofibromin-dependent dopaminergic signaling in a subject having or suspected of having neurofibromatosis type 1 (NF1).

Suitably, the expression level of the neurofibromin in the sample obtained from the subject is reduced when analyzed against the reference expression level as described herein.

The method can further include identifying an expression level of dopamine Suitably, the expression level of the dopamine in the sample obtained from the subject is reduced when analyzed against the reference expression level as described herein.

The method can further include identifying phosphorylation of dopamine and cAMP regulated neuronal phosphoprotein (DARPPP-32). Suitably, the phosphorylation of DARPPP-32 in the sample obtained from the subject is reduced when analyzed against the reference expression level as described herein.

The method can further include detecting a point mutation in an exon of the Nf1 gene. The Nf1 gene can be a human Nf1 gene (see, Accession No. NM_00104292.2) and a mouse Nf1 gene (see, Accession No. NM_010897.2). Suitable exons in which a point mutation can be detected can be exon 18, exon 21, and combinations thereof. A particularly suitable point mutation to be detected in exon 18 is c.2041C>T of the human Nf1 gene (see, Accession No. NM_00104292.2). A particularly suitable point mutation to be detected in exon 21 is c.2542G>C of the human Nf1 gene (see, Accession No. NM_00104292.2).

Suitable samples can be brain, hippocampi, peripheral white blood cells, skin, and combinations thereof.

Suitable subjects can be any vertebrate species. Particularly suitable subjects can be humans and rodents as described herein. Particularly suitable human children include children having or suspected of having neurofibromatosis type 1 (NF1).

EXAMPLES

Materials and Methods

Mice.

All animals were maintained on an inbred C57BL/6 background using a 12 hour light/dark cycle with ad libitum access to food and water. Heterozygous Nf1 mice were generated with one wild-type copy of the Nf1 gene and one copy containing either a missense mutation in exon 21 (corresponding to the human c 2542G>C NF1 gene mutation; p.G848R) ($Nf1^{+/sp21}$), a nonsense mutation in exon 18 (corresponding to the human c 2041C>T NF1 gene mutation; p.R681X) ($Nf1^{+/st18}$) or a null inactivating allele created by the insertion of a neomycin cassette within exon 31 ($Nf1^{+/neo31}$, $Nf1^{+/-}$). Conditional knockout mice were generated with the sp21, neo31 or st18 mutation as the germline Nf1 allele, with somatic Nf1 gene inactivation resulting from Cre-mediated excision of an Nf1flox allele in neuroglial progenitor cells. The resulting strains included $Nf1^{GFAP}$ flox/sp21 (Nf1 flox/sp21; GFAP-Cre, F21C), $Nf1^{GFAP}$ flox/− (Nf1 flox/neo31; GFAP-Cre, FMC and $Nf1^{GFAP}$ flox/st18 (Nf1 flox/st18; GFAP-Cre, F18C). Littermate $Nf1^{+/+}$ and $Nf1^{flox-flox}$ (FF) mice were used as controls. All experiments were performed on 3-month-old animals, unless otherwise stated, under active Animal Studies Committee protocols at the Washington University School of Medicine.

White Blood Cell Isolation.

1-3 mL of fresh mouse peripheral blood was collected from 3-month-old mice by retro-orbital bleed into EDTA-coated vials. An equal volume of PBS was added to the blood before the solution was layered over 3 mL of Ficoll-Paque and fractionated by centrifugation to isolate the white blood cell (WBC) layer. WBCs were further washed by centrifugation, and the resulting cell pellet was snap-frozen and stored at −80° C. A minimum of 10 animals per genotype was used for WBC protein analysis.

Western Blotting, Immunohistochemistry and Immunofluorescence.

Western blotting was performed on snap-frozen hippocampi or WBC pellets, lysed in RIPA buffer supplemented with protease inhibitors as previously described (Brown et al, 2010) using appropriate primary antibodies (Table 1), secondary horseradish peroxidase-conjugated antibodies (Sigma, St. Louis, Mo.) and ECL (Fisher) chemiluminescence. Western signal band intensity was quantified using ImageJ Software (National Institutes of Health, USA) Immunohistochemistry and immunofluorescence were performed as previously described (Brown et al, 2010), on mice transcardially perfused with 4% PFA (Sigma) in 0.1 M sodium phosphate buffer (pH 7.4) and post-fixed in 4% PFA prior to paraffin embedding. For some immunofluorescence experiments (Brn3a, Ccl5), amplification of the antibody signal was performed using the TSA Cy3 Plus system (Perkin Elmer) as previously described (Kaul, Toonen 2014). A minimum of 5 animals per genotype was used for these analyses.

TABLE 1

Primary Antibodies.

| Antibody | Source | Host animal | Dilution | Application |
|---|---|---|---|---|
| Neurofibromin | Santa Cruz (sc-67) | Rabbit | 1:100 | WB |
| Phospho-DARPP-32 (Thr34) | Santa Cruz | Goat | 1:100 | WB |
| DARPP-32 | Cell Signaling | Rabbit | 1:500 | WB |
| RAS (Clone RAS10) | Millipore | Mouse | 1:1,000 | WB |
| α-Tubulin | Life Technologies | Mouse | 1:20,000 | WB |
| Iba1 | Wako | Rabbit | 1:1,000 | IHC |
| Phospho-Akt (Thr308) | Cell Signaling | Rabbit | 1:1000 | IHC |
| Phospho-Akt (Ser473) | Cell Signaling | Rabbit | 1:1000 | IHC |
| phospho-S6 S240/244 | Cell Signaling | Rabbit | 1:1000 | IHC |
| Phospho-SAPK/JNK | Cell Signaling | Rabbit | 1:1000 | IHC |
| Ccl5 | Lifespan Biosciences | Rabbit | 1:150 | IF |
| GFAP | Invitrogen | Rat | 1:200 | IHC |
| Brn3a | Santa Cruz | Mouse | 1:500 | IF |
| SMI-32 | Covance | Mouse | 1:500 | IHC |
| cAMP | Abcam | Mouse | 1:1000 | IF |
| Ki67 | | | | IHC |

RAS Activity, cAMP and Dopamine Assays.

Snap-frozen adult mouse hippocampi were used to perform RAS activity (Millipore), dopamine (Rocky Mountain Diagnostics) and cAMP (Enzo Life Sciences) assays. Active Ras (Ras-GTP) was detected by Raf1-RBD immunoprecipitation using the RAS activation kit according to the manufacturer's instructions. Samples processed for cAMP and dopamine ELISA assays were homogenized in ice-cold 0.1M HCl pH7.4 and levels quantitated as previously reported (Anastasaki et al., 2015 PMID: 25788518, Diggs-Andrews et al., 2014).

Behavioral Testing.

For Morris Water Maze testing, mice underwent trial sessions for two consecutive days, where they were trained in a water maze with a visibly-marked, but variably-placed, platform (cued trials). Additionally, mice were trained for 5 consecutive days in a water maze with a hidden platform that had a static location (place trials). Memory retrieval was analyzed in the same water maze 1 hour after the end of the last place trial on the third and fifth days, when the hidden platform was removed. The escape path length (distance traveled to platform) as well as the swimming speed and latency (swimming time to platform) were recorded for all training and probe trials. The time spent in the water maze quadrant containing the former location of the platform (target quadrant) and the spatial bias for the target quadrant (time in target versus other quadrants) were used as readouts for the probe trials. Ten animals per genotype were used for these analyses.

Primary Astrocyte Culture and Proliferation Assay. Primary astrocytes were generated from the brainstems of postnatal day 0-1 mouse pups and maintained in astrocyte growth medium (Dulbecco's Modified Eagle's medium (DMEM) containing 10% fetal bovine serum and 0.01% penicillin/streptomycin). To inactivate the conditional Nf1$^{flox}$ allele, astrocytes (passage 1) were infected with adenovirus type 5 (Ad5) containing Cre recombinase (Ad5-Cre) (University of Iowa Gene Transfer Vector Core, Iowa City, Iowa). Control infections employed Ad5 containing β-galactosidase (Ad5-LacZ). 4 days post-infection, astrocytes were passaged and serum-starved for 48 h prior to Western blotting and proliferation analysis. Astrocyte proliferation was assessed using the BrdU Cell Proliferation ELISA kit (Roche) following manufacturer's instructions. Briefly, 6,000 serum-starved astrocytes were labeled with BrdU for 18 hours followed by a 2-hour incubation in peroxidase-conjugated anti-BrdU antibody. Proliferating astrocytes were identified using a colorimetric substrate reaction measured at 450 nM on a spectrophotometer (Bio-Rad).

Statistical Analysis.

All statistical analyses were performed using GraphPad Prism 5 software (GraphPad Software). Unpaired two-tailed Student's T-tests were used for experiments analyzing data between two groups. One-way or two-way ANOVA with Bonferroni post-test correction analyses were employed for multiple comparisons.

Optic Nerve Volume Measurements.

Optic nerves with an intact chiasm were microdissected following transcardial perfusion. Optic nerves were photographed and diameters measured at the chiasm (~150, ~300, and ~450 microns anterior to the chiasm) to generate optic nerve volumes. A minimum of five animals per genotype was employed for the measurement of optic nerves.

Retinal Nerve Fiber Layer Measurements.

Retinal nerve fiber layer (RNFL) thickness was quantitated using the average of 15 measurements of SMI-32-stained axons 0-250 μm proximal to the optic nerve head (ImageJ software). A minimum of five animals per genotype was used for this analysis.

Example 1

In this Example, the effect of specific Nf1 germline mutations on optic glioma formation was analyzed.

Figure 1B:
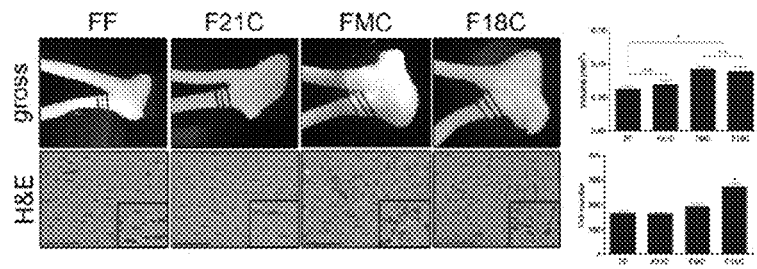
Figure 1C:
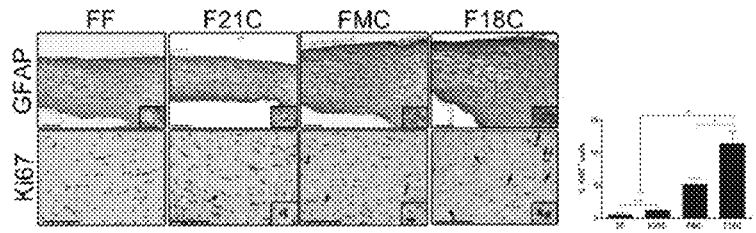

C57/B16 mice that harbor germline point mutations in exons 21 (sp21) and 18 (st18) were generated. Employing the GFAP-Cre driver line, we generated two new conditional knockout (CKO) mice that have a single germline mutation in all cells and an additional somatic inactivating mutation in neuroglial cells: 2542G>C (exon 21; Nf1 flox/21 GFAP-Cre; F21C) and 2041C>T (exon 18; Nf1 flox/18 GFAP-Cre; F18C) (FIG. 1A). Direct volume measurements of optic nerves revealed a 43% increase in optic nerve volumes of F18C mice, similar to Nf1$^{flox/-}$ GFAP-Cre (FMC; Bajenaru et al, 2003 PMID: 14695164) mice (48% increase), whereas there was no significant increase in optic nerve volume of F21C mice compared to FF controls (FIG. 1B). Additionally, hematoxylin and eosin staining revealed hypercellularity (1.6 fold increase in cell number), mitotic figures and atypical cells in F18C optic nerves, whereas F21C optic nerves were indistinguishable from controls (FIG. 1B) Similarly, an increase in GFAP immunoreactivity was only found in FMC and F18C optic nerves compared to FF controls (FIG. 1C). GFAP immunoreactivity was significantly elevated in F18C compared to FMC mice. Together, these data suggest that tumor formation is Nf1 germline mutation-dependent.

Figure 1D:
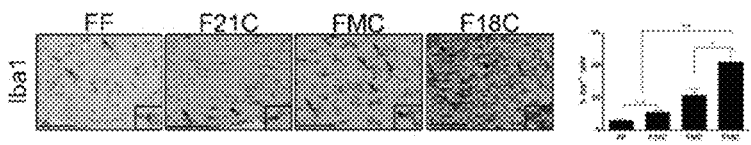
Figure 1E:
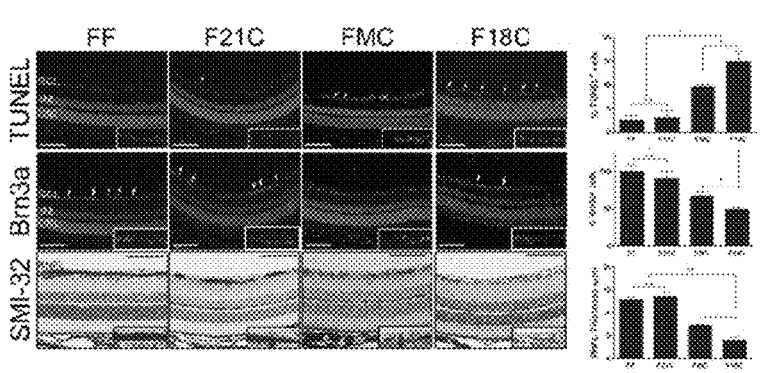

Most children with NF1-OPG come to clinical attention due to vision loss. In fact, up to half of children with NF1-OPG succumb to loss of visual acuity. Previous studies from have shown differential loss of retinal ganglion cells (RGCs) due to tumor aggressiveness (Kaul et al, 2014 PMID 25246427). That the increased tumor growth in F18C mice may have worsened retinal dysfunction was determined. In that respect, a 1.5 fold increase in TUNEL$^+$ cells and a 27%±6.5 reduction of Brn3a+ retinal ganglion cells in F18C retinae was found as compared to FMC and FF controls (FIG. 1E). Moreover, optical coherence tomography (OCT) has been a useful, non-invasive clinical tool to demonstrate retinal nerve fiber layer (RNFL) thinning in NF1 patients with loss of visual acuity. RNFL thickness was visualized by axon immunostaining for SMI-32 in F18C mice compared to FMC, F21C and controls. Thinning was identified only in FMC and F18C mice (FIG. 1E). F18C had further RNFL thinning compared to FMC mice. Taken together, these data suggest that visual acuity is highly sensitive to Nf1 germline mutation.

Ki67 immunostaining revealed a significant increase in proliferation in F18C mice compared to FF controls (2.2-fold) as well as to FMC mice (2.17-fold) (FIG. 1C). Conversely, there was no significant increase in Ki67+ cells in F21C optic nerves. To further determine if astrocyte proliferation was impacted by sp21 and st18 germline mutations upon Nf1 inactivation in a cell-autonomous manner, primary astrocytes were cultured from heterozygous Nf1$^{flox/sp21}$, Nf1$^{flox/-}$, Nf1$^{flox/St18}$ brainstem tissue and were either infected with a control virus containing β-galactosidase (LacZ) or Cre recombinase (Cre) (LacZ) (FIG. 6). Upon bi-allelic mutation of Nf1 (F21C; FMC; F18C), astrocyte proliferation was similarly increased in all three groups (1.3-2-fold). Collectively, these data suggest that the specific heterozygous glioma microenvironment is responsible for the observed increase in proliferation in F18C mice in vivo compared to control and F21C mice.

Example 2

In this Example, the effect of Nf1 germline mutation on microglial infiltration and signaling was analyzed.

Figure 7A:
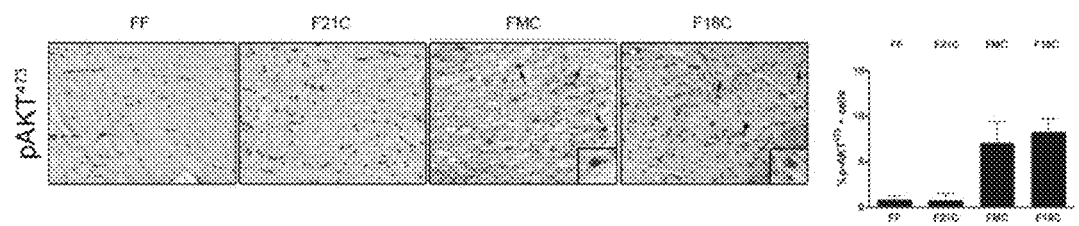
FIGS. 7A & 7B depict activation of Nf1-mTOR pathway in FMC and F18C optic gliomas.
Figure 7B:
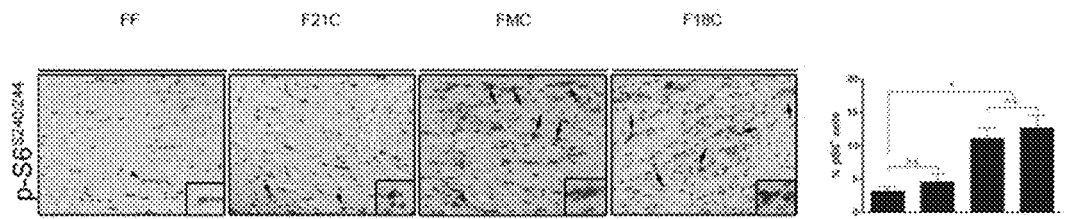

Non-neoplastic cells in the optic glioma microenvironment, such as Nf1 microglia, contribute to tumor formation, growth and maintenance by promoting astrocyte proliferation. In accordance with these findings, an increase in F18C optic nerve microglia (97%± 7) was found, but not in F21C optic nerves compared to FMC mice (FIG. 1D) indicating that the specific Nf1 germline mutation contributes to microglia activation and infiltration. Since inactivation of the second Nf1 allele promoted higher proliferation in all astrocyte cultures irrespective if the Nf1 germline mutation (FIG. 6), whether optic nerve tumor formation in FMC and F18C mice is dependent on microglial infiltration and activation rather than astrocyte proliferation was analyzed. Previous studies have revealed that JNK pathway activation (phospho JNK) in microglia is critical for optic nerve formation and maintenance Immunohistochemical staining showed increased levels of pJNK in optic nerve gliomas of FMC and F18C animals compared to controls (FIG. 2A). Similar to Iba1 staining, F18C optic nerves exhibited significantly higher JNK activation than FMC mice. Additionally, recently published work revealed that tumor associated microglia secrete CLL5 in order to promote glioma formation. As such, significantly elevated CCL5 (FIG. 2B) was observed in F18C when compared to FMC optic nerve gliomas. Finally, CCL-5 can promote activation of Akt through phosphorylation of Ser308. Since this site is phosphorylated independently of the RAS-mTOR pathway which is activated in FMC optic gliomas (FIG. 7), activation of pAkt$^{Ser308}$ in optic nerves of the three mouse models was examined pAkt$^{Ser308}$ was only significantly elevated (2.9-fold) in F18C optic nerves (FIG. 2C), indicating that the Nf1 St18 mutation promotes tumor formation and increased microglia infiltration in an Nf1-pJNK-CCL5-pAkt$^{308}$-dependent manner.

Figure 8:
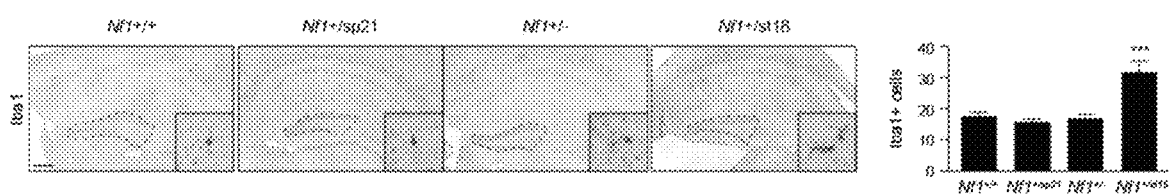
FIG. 8 depicts higher microglia infiltration in Nf1$^{+/-st18}$ hippocampi. Immunostaining (images in left panel) and Iba1$^+$ cells (graph in right panel) with Iba1 reveals significantly higher number of Iba1 positive microglia in the hippocampi of Nf1$^{+/-st18}$ mice compared to Nf1$^{+/+}$ (WT), Nf1$^{+/sp21}$ and Nf1$^{+/-}$ mice. Data are represented as means±s.e.m. (**P<0.001; *P<0.0.01; One-way ANOVA with Bonferroni post-test).
Figure 9A:
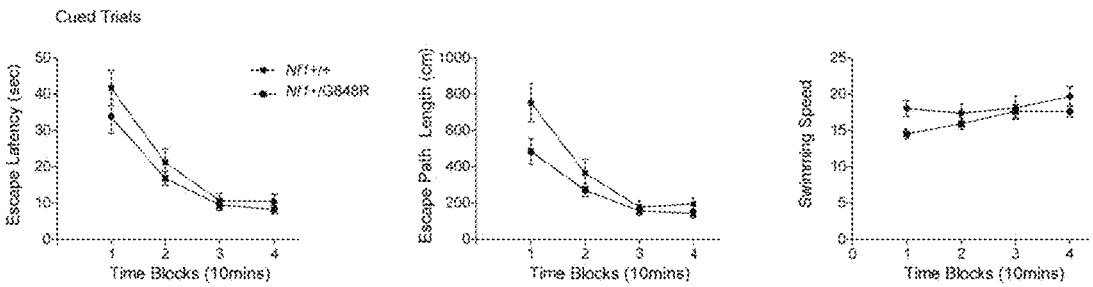
FIGS. 9A-9D depict behavioral analysis of Nf1$^{+/sp21}$ and Nf1$^{+/st18}$ WT mice, Nf1$^{+/st18}$ mice, WT mice and Nf1$^{+/sp21}$ mice. Nf1$^{+/st18}$ WT mice and Nf1$^{+/st18}$ mice (FIGS. 9A & 9B), WT mice and Nf1$^{+/sp21}$ mice (FIGS. 9C & 9D) spent similar time swimming, covered a similar total distance, and exhibited swimming speeds during the cued (FIGS. 9A & 9C) and place (FIGS. 9B & 9D) training trials.
Figure 9B:
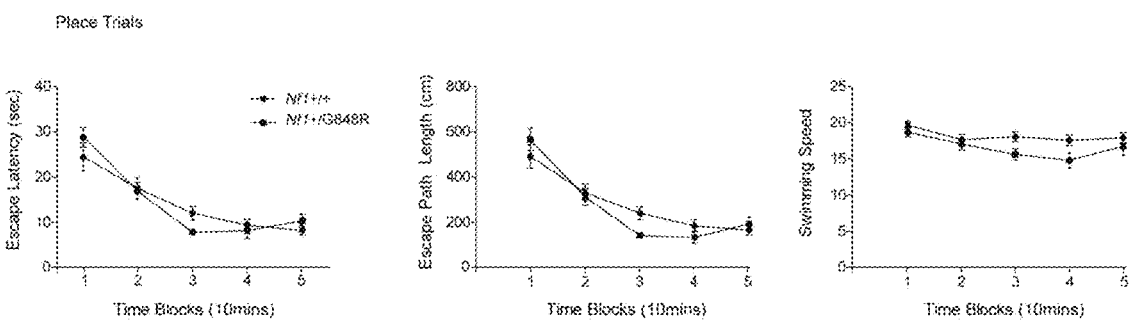
Figure 9C:
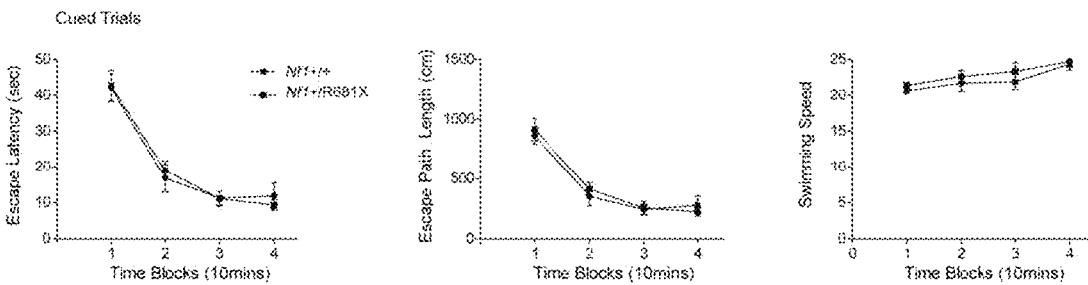
Figure 9D:
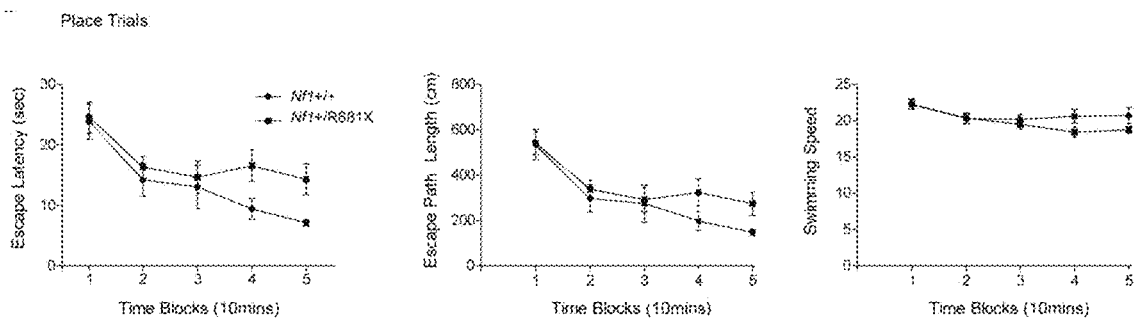

Finally, since microglia are affected by the specific Nf1 germline mutation, microglial infiltration of the optic nerve of mice that harbor only a germline Nf1 mutation: Nf1+/sp21, Nf1+/− and Nf1+/st18 mice were examined Immunohistochemical staining with Iba1 revealed a significant increase in microglia numbers in the optic nerves (FIG. 2D) only of Nf1+/−st18 animals compared to the other two Nf1 mutant mice and wild-type controls. Moreover, a significantly (P<0.0001) higher number of microglia were observed in the hippocampi of the same animals (FIG. 8). Collectively, these data suggest that microglia infiltration is highly sensitive to the specific Nf1 germline mutation.

Example 3

In this Example, the dependence of Nf1 germline mutation on Neurofibromin expression levels were analyzed.

Figure 3A:
FIGS. 3A-3C depict NF1 germline mutation dependence of neuronal neurofibromin expression.

Similarly to microglia, neurons are highly sensitive to Nf1 germline mutation. As such, NF1 germline mutation impacts neuronal signaling both in human NPCs and mouse hippocampal neurons. To determine the effect of specific Nf1 germline mutations on mouse neurons, neurofibromin expression levels were assayed in hippocampi of Nf1+/sp21, Nf1+/− and Nf1+/st18 animals (FIG. 3A). Western blotting revealed that neurofibromin expression was decreased by 39% in Nf1+/−sp21, 50% in Nf1+/− and 76% in Nf1+/st18 hippocampi.

Figure 3B:
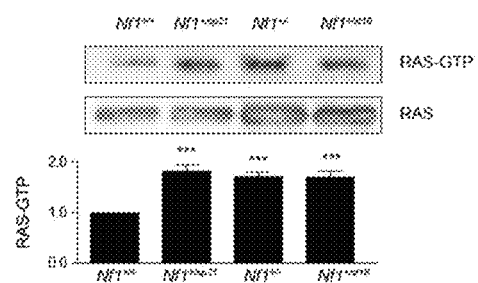
Figure 3C:

To further assess whether the specific germline mutation differentially impacted neurofibromin GAP activity in the three Nf1 models RAS activity (RAS-GTP) in adult mouse hippocampi were assayed. RAS activity was increased by 1.8-fold in Nf1+/sp21, 1.7-fold in Nf1+/− and 1.7-fold in Nf1+/st18 hippocampi (FIG. 3B). Since RAS negatively regulates cAMP in Nf1-depleted neurons, cAMP levels were measured in the three mouse models. cAMP levels were decreased by 49% in Nf1+/sp21, 51% in Nf1+/− and 52% in Nf1+/st18 hippocampi (FIG. 3C). Thus, similar to human iPSC-NPs, where RAS-cAMP regulation is NF1 dosage-independent, Nf1-RAS-dependent signaling in CNS mouse neurons was not sensitive to neurofibromin expression levels.

Example 4

In this Example, regulation of spatial memory in mice by neurofibromin was analyzed.

Figure 4A:
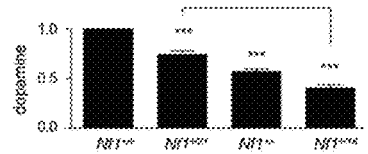
FIGS. 4A-4D depict elicitation of memory deficit in Nf1+/st18 mice by Nf1 germline mutation.
Figure 4B:
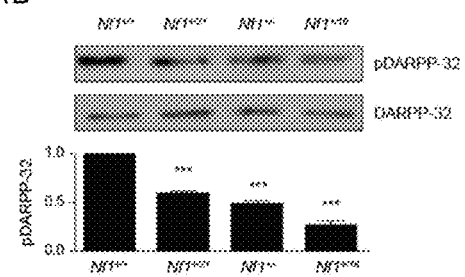

Unlike RAS-driven phenotypes, dopamine (DA) signaling, phosphorylation of dopamine and cAMP regulated neuronal phosphoprotein (DARPP-32) is regulated by neurofibromin levels. To this end, DA levels in all Nf1+/− mice were assayed and established that DA was decreased by 38% in Nf1+/sp21, 50% in Nf1+/− and 64% in Nf1+/st18 hippocampi (FIG. 4A), correlating with neurofibromin levels ($R^2$=0.9748) (FIG. 4E). In addition, DARPP-32 activity (pDARPP-32) was decreased by 44%, in Nf1+/sp21, 51% in Nf1+/− and 77% in Nf1+/st18 hippocampi (FIG. 4B), highly correlating with respective neurofibromin expression ($R^2$=0.9835) (FIG. 4F).

Figure 4C:
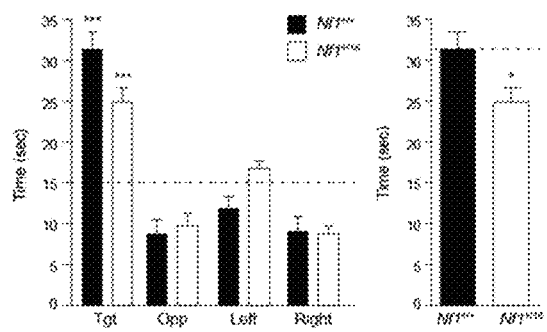
Figure 4D:
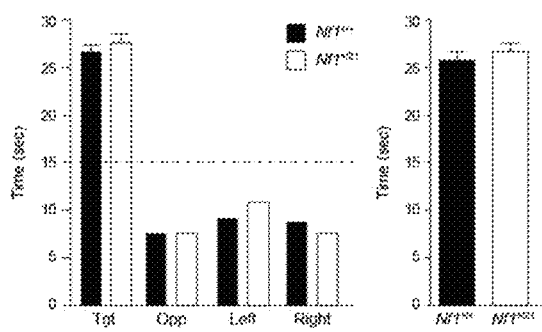
Figure 4E:
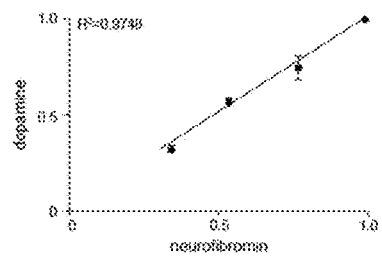
FIGS. 4E & 4F depict the correlation of relative neurofibromin expression and DA levels (R2=0.9748) (FIG. 4E) or pDARPP-32 levels (R2=0.9835) (FIG. 4F) in Nf1 $^{+/-}$ hippocampi. All data are represented as means±s.e.m.
Figure 4F:
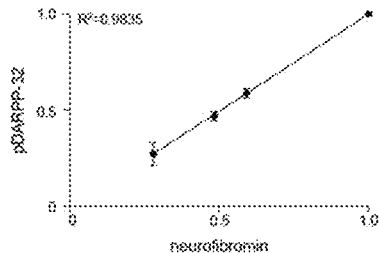

Since neurofibromin-dependent dopamine homeostasis and signaling are particularly important in regulating hippocampal-based memory, the performance of Nf1 mutant mice was tested in the Morris water maze (FIGS. 4C & 4D). All animals were able to identify the location of a hidden platform and performed similarly during the "cued" and "place" trials, indicating their intact ability to learn the spatial task (FIG. 9). Moreover, during the "probe" trials of the water maze, Nf1+/sp21 showed no memory deficits compared to WT controls (FIG. 4D). However, Nf1+/st18 mice spent significantly less time in the target quadrant, indicating a deficit in memory retrieval compared to control mice.

Figure 10A:
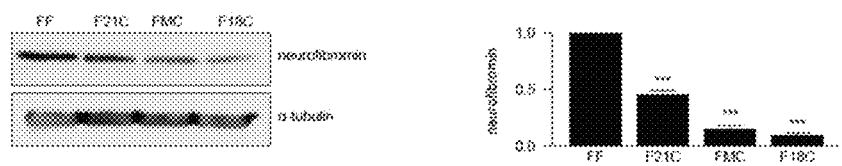
FIGS. 10A-10F depict the effect of Nf1 germline mutation on Neurofibromin/pDARPP-32 dependent spatial memory.
Figure 10B:
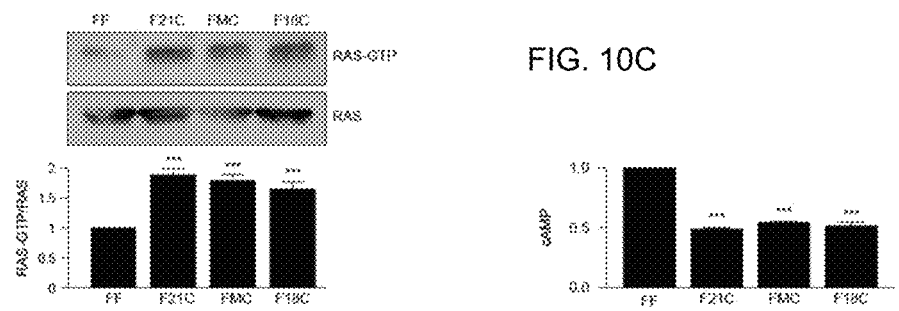
Figure 10C:
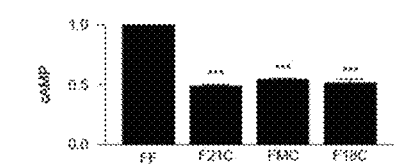
Figure 10D:
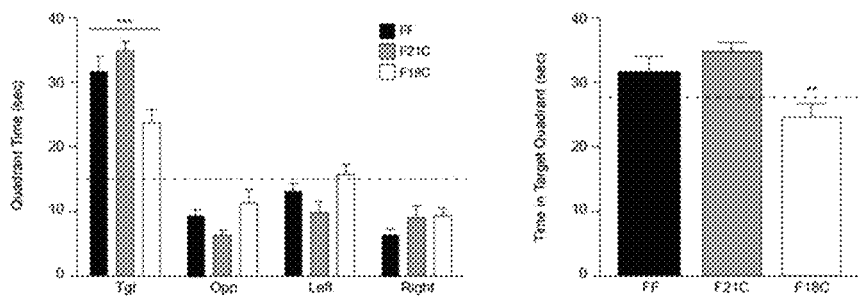
Figure 10E:
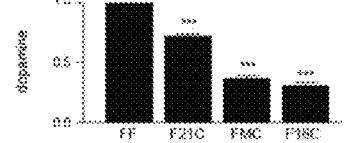
Figure 10F:
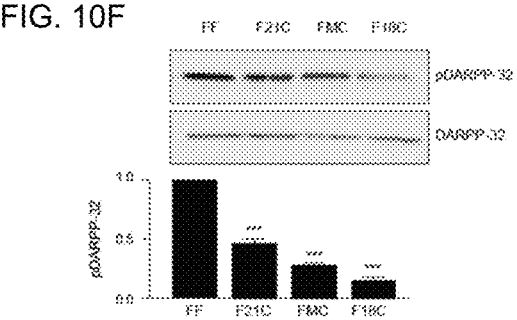
Figure 11A:
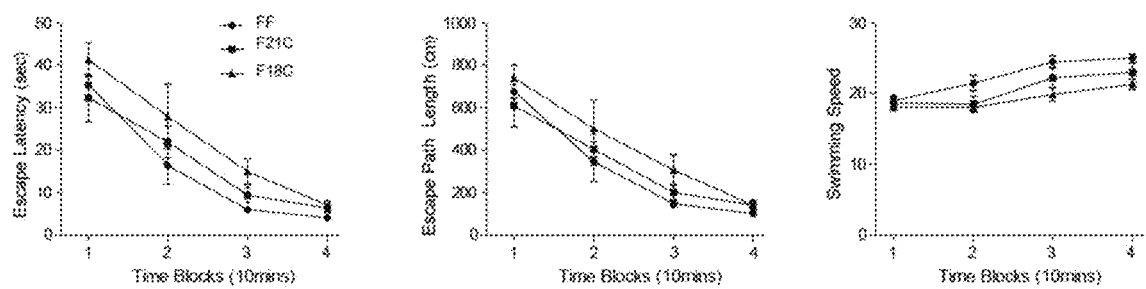
FIG. 11A & 11 B depict the behavioral analysis of Nf1 CKO mice. WT, F21C and F18C mice spent similar time swimming, covered a similar total distance and exhibited similar swimming speeds during the cued (FIG. 11A) and place (FIG. 11B) training trials.
Figure 11B:
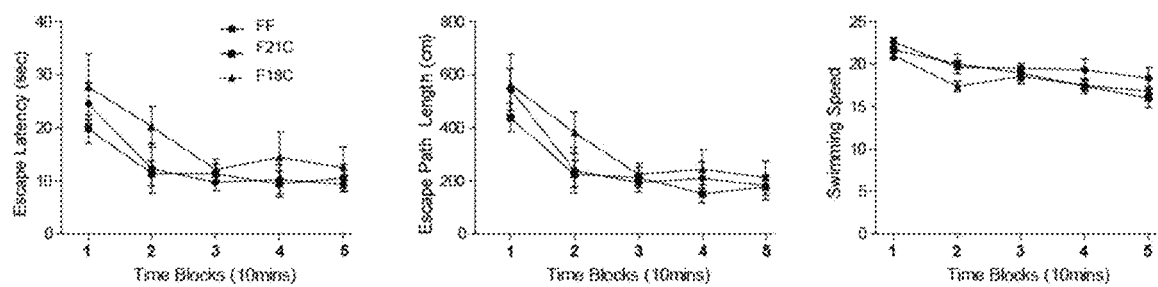

Consistent with the findings in hemizygous Nf1+/− mice, inactivation of the second Nf1 allele reduced neurofibromin levels in hippocampi of F21C, FMC and F18C mice by 52%, 73% and 82% respectively compared to FF controls (FIG. 10A) Similarly, DA levels as well as pDARPP-32 were decreased in a neurofibromin dose-dependent manner (FIGS. 10E & 10F). As such, pDARPP-32 levels were decreased by 52% in F21C, 74% in FMC and 83% in F18C hippocampi (FIG. 10F). Moreover, only F18C mice exhibited a spatial memory deficit in the Morris water maze (FIG. 10D), further underscoring the importance of Nf1 germline mutation-driven neurofibromin levels in eliciting behavioral phenotypes.

Example 5

In this Example, Neurofibromin, DA and pDARPP-32 were analyzed as biomarkers of brain neuronal function.

Figure 5A:
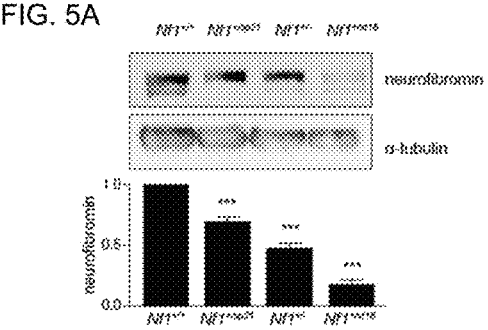
FIGS. 5A-5H depict prediction of brain dopaminergic signaling with blood biomarkers.
Figure 5B:
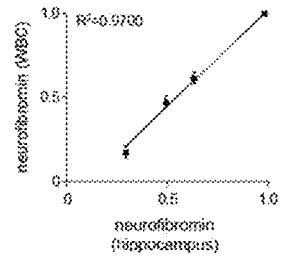
Figure 5C:
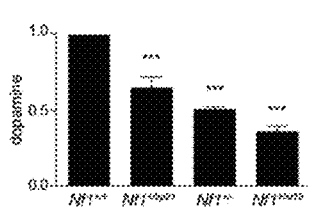
Figure 5D:
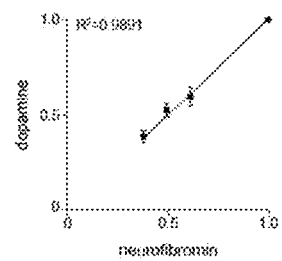
Figure 5E:
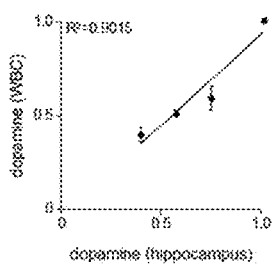
Figure 5F:
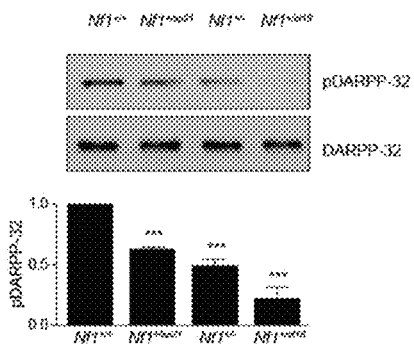
Figure 5G:
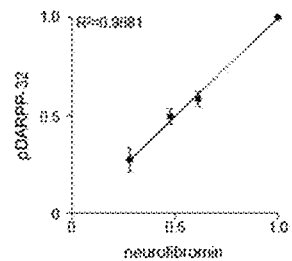
Figure 5H:
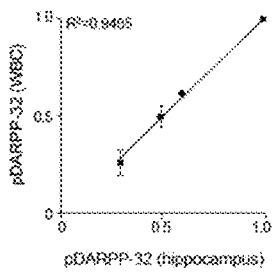

To assess whether peripheral neurofibromin, DA and pDARPP-32 can be used as biomarkers of brain neurofibromin-dependent dopaminergic signaling, white blood cells (WBC) were isolated from peripheral blood of Nf1 heterozygous mice (FIG. 5A). Upon neurofibromin immunoblotting, a significant correlation ($R^2_{Nf1}$=0.9700) between WBC and hippocampal neurofibromin levels was observed (FIG. 5B). Similarly, DA concentration in WBC correlates (FIG. 5C) with WBC neurofibromin ($R^2$=0.9891) (FIG. 5D) and hippocampal DA ($R^2$=0.9015) (FIG. 5E). Finally, DARPP-32 phosphorylation in leukocytes (FIG. 5F) correlates with WBC neurofibromin ($R^2_{Nf1}$=0.9881) (FIG. 5G) and is highly predictive of hippocampal pDARPP-32 ($R^2$=0.9465) (FIG. 5H). Collectively these data establish neurofibromin, DA and pDARPP-32 as novel blood biomarkers of memory defects in Nf1 models.

Example 6

In this Example, neurofibromin levels were analyzed in patients diagnosed with NF1.

Thirteen adult patients diagnosed with NF1 using NIH Consensus Development Conference diagnostic criteria who receive their medical care in the Washington University in St. Louis Children's Hospital Neurofibromatosis Clinical Program were randomly selected and underwent a skin punch biopsy under an approved Human Studies Protocol at the Washington University School of Medicine. A collection of primary fibroblast lines was established using unrelated male (n=5) and female (n=8), as well as from four sex- and age-matched control individuals with no known neurological problems. The specific germline NF1 gene mutation was identified following mutational analysis of DNA and RNA extracted from primary skin fibroblasts using an RNA-core assay complemented with dose analysis by multiplex ligation-dependent probe amplification (MLPA) as described in Messiaen, L. M. W. (In Monogr. Hum. Genet. Karger, Basel, D, K. (ed.), 2008, 16:63-77). NF1 gene nucleotide numbering is based on GenBank reference sequence NM_000267.3 and protein numbering based on NP_000258.1. Exon numbering was assigned according to the NCBI reference sequence along with the known legacy numbering in parenthesis. Nomenclature of the mutations follows the recommendations of the Human Genome Variation Society.

Primary fibroblasts were isolated and cultured from plated skin biopsies collected from patients with NF1 and control individuals for ~3 weeks. Established lines were reprogrammed into iPSCs using Cyto-Tune technology (Invitrogen). Confluent fibroblasts were infected with a Sendai virus carrying four stem cell reprogramming factors (OCT4, KLF4, SOX2, C-MYC). Six weeks later, iPSC colonies were isolated and their pluripotency confirmed by morphological assessment and the expression of stem cell markers (Nanog, SOX2, OCT4, SSEA-4, TRA-1-60, TRA-1-81). Chromosomal analysis demonstrated normal karyotypes in al lines. Two separate clones from each iPSC line were cultured in Neural Induction Medium (NIM; STEMCELL Technologies) for 5 days. Embryoid body aggregates were plated in NIM on adhesive plates pre-coated with poly-ornithine/laminin Once neural rosettes formed, gentle dissociation and replating facilitated their differentiation into NPCs. A portion of NPCs were differentiated into dopaminergic neurons.

Western blotting was performed using appropriate primary antibodies, secondary horseradish peroxidase-conjugated antibodies (Sigma) and CL (Fisher) chemiluminescence. Neurofibromin (C) antibody (sc-67) was used instead of neurofibromin (N) (sc-68) unless otherwise specified Immunocytochemistry was performed on 4% paraformaldehyde (PFA) fixed cultured cells.

Figure 12A:
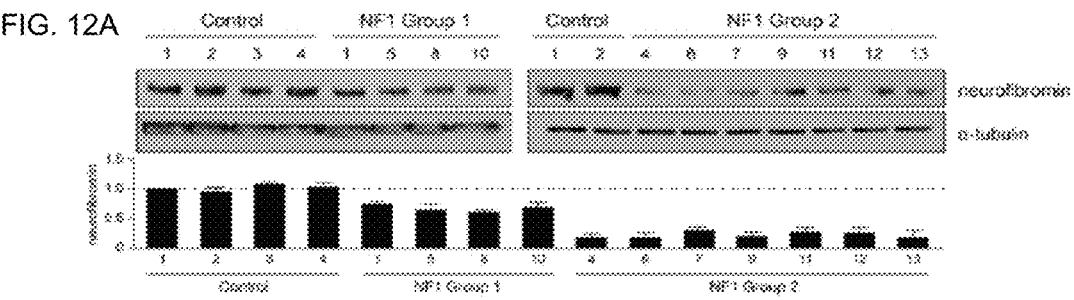
FIG. 12A-12C depict that germline NF1 gene mutations result in differences in neurofibromin expression in NF1-patient fibroblasts.
Figure 12B:
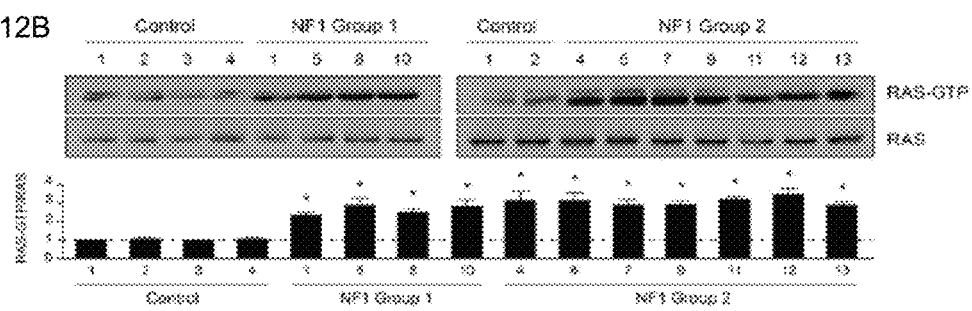

Analysis of neurofibromin levels revealed two distinct subgroups (FIG. 12A): those with minor reductions (Group 1; <25% following normalization to α-tubulin) and those with >70% reductions (Group 2) in neurofibromin expression. This differential neurofibromin expression pattern was observed using both carboxyl- and amino-terminal neurofibromin antibodies and was not related to NF1 RNA expression levels nor to patient sex, age or the in vitro growth conditions employed (with or without serum; data not shown). In all NF1-patient fibroblasts, there was increased RAS activity (FIG. 12B) relative to control patient fibroblasts.

Figure 12C:
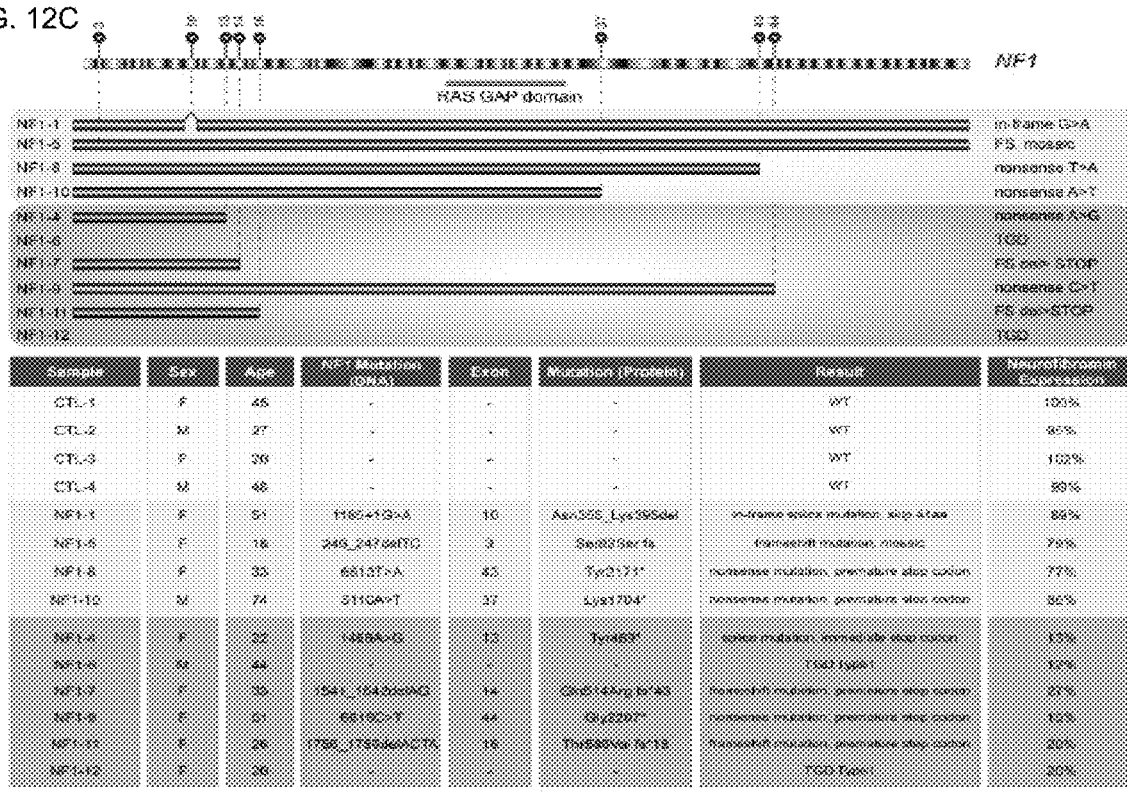

To determine whether these differences in neurofibromin protein expression reflected the underlying germline NF1 gene mutation, all NF1-patient fibroblast samples were analyzed (FIG. 12C). In these individuals, 10 distinct mutations were conclusively identified. The mutations in Group 1 causing mild reductions in neurofibromin expression were frameshift (NF1-1, NF1-5) or nonsense mutations (NF1-8, NF1-10) and the mutations in Group 2 with more dramatic reductions in neurofibromin expression included nonsense mutations (NF1-4, NF1-7, NF1-9, NF1-11) and large microdeletions of the NF1 locus (NF1-6, NF1-12). These data indicate that there is no apparent correlation between the location or nature of the germline NF1 mutation and the level of neurofibromin expression.

Figure 13A:
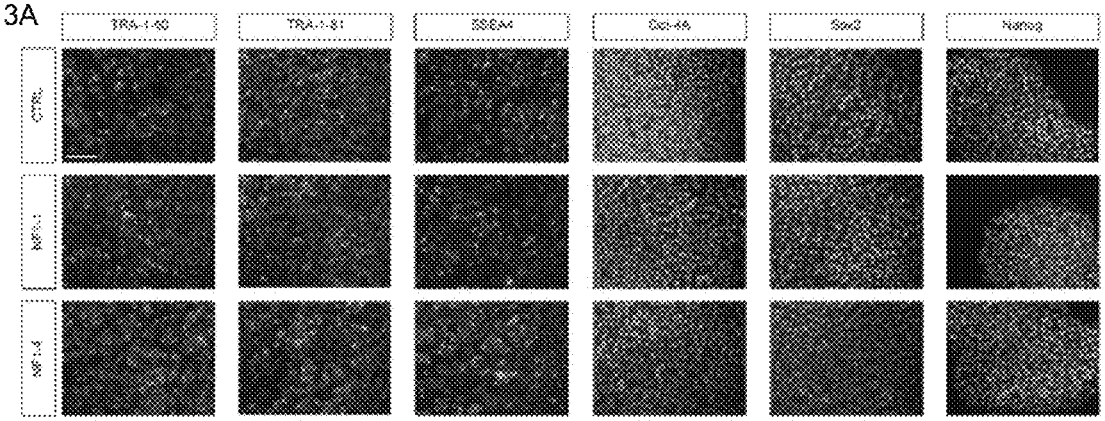
FIG. 13A-13D depict that germline NF1 gene mutations promote differential neurofibromin expression in NF1-patient-derived iPSCs.
Figure 13B:
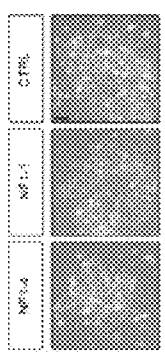
Figure 13C:
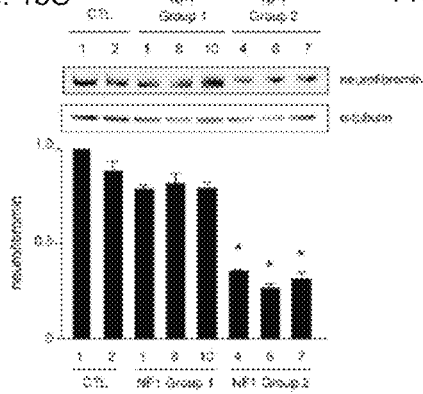
Figure 13D:
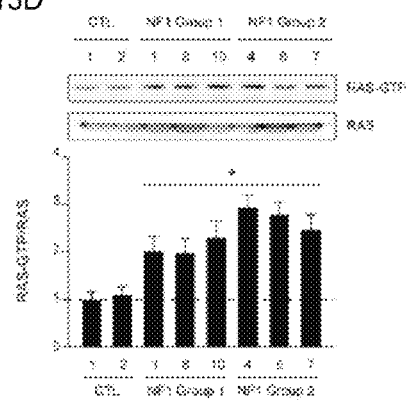

Leveraging induced pluripotent stem cell (iPSC) technology and integration-free Sendai virus infection, primary skin fibroblasts were reprogrammed into iPSCs (FIG. 13A). Following immunoblot analysis, the same differential pattern of neurofibromin expression in fibroblasts was observed in the derivative iPSCs (FIG. 13C). Consistent with its established role as negative RAS regulator, the levels of active RAS (RAS-GTP) were elevated in all NF1-iPSCs, irrespective of neurofibromin levels (FIG. 13D), similar to the results in NF1-patient fibroblasts.

Figure 14A:
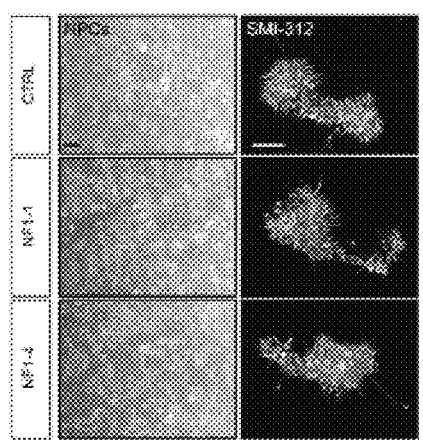
FIG. 14A-14D depict that germline NF1 gene mutations promote differential neurofibromin expression in NF1-patient-derived NPCs.
Figure 14B:
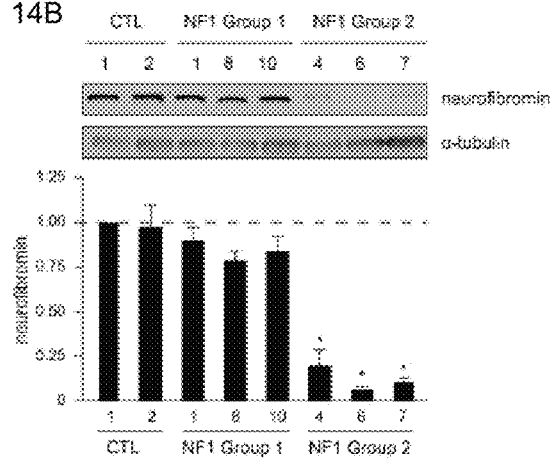
Figure 14C:
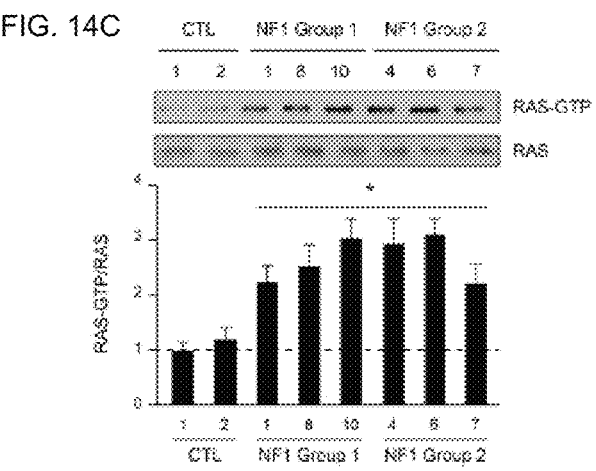
Figure 14D:
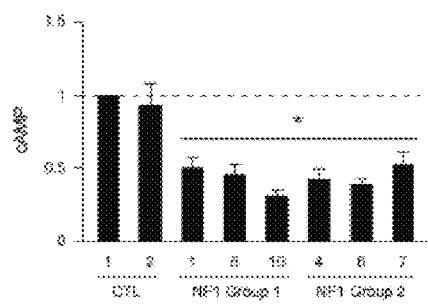

To examine the effect of the germline NF1 gene mutation on central nervous system lineage cells, iPSC were directed differentiate into neural progenitor cells (NPCs) (FIG. 14A). The neurofibromin expression observed similarly matched the patterns found in the parental fibroblasts and iPSCs (FIG. 14B). Previous work revealed that neurofibromin positively controls cyclic AMP (cAMP) in a RAS-dependent manner in brain neurons. Consistent with this mechanism, all NF1-NPCs exhibited 2-3-fold elevated RAS-GTP levels (FIG. 14C), irrespective of the germline NF1 gene mutation. Similarly all NF1-NPCs showed significantly reduced cAMP (>50%) levels relative to control NPCs (FIG. 14D).

Figure 15A:
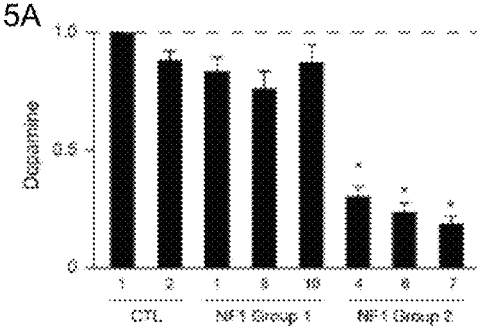
FIG. 15A-15D depict that germline NF1 gene mutations regulate dopamine signaling in a gene dose-dependent manner in NF1-patient NPCs.
Figure 15B:
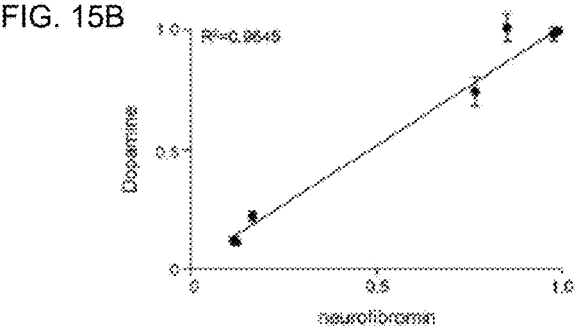
Figure 15C:
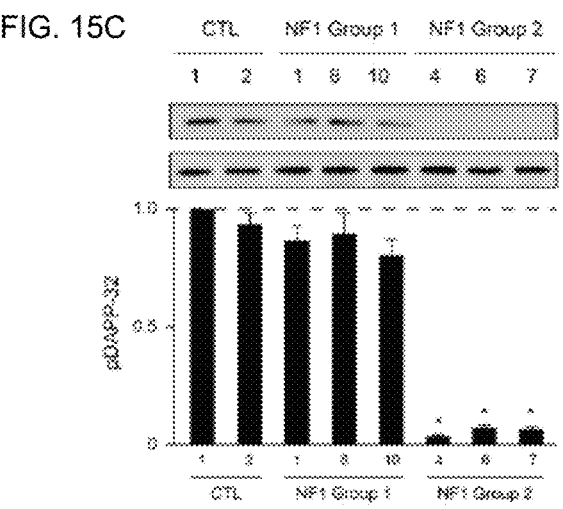
Figure 15D:
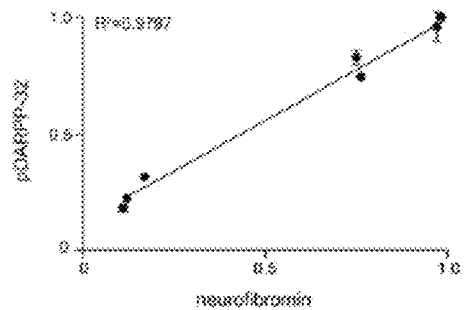

In contrast, neurofibromin control of DA homeostasis in the striatum and hippocampus is RAS-independent. As such, Group 1 NF1-NPCs exhibited <25% reductions in DA levels, while Group 2 NF1-NPCs had ~75% reductions (FIG. 15A). Importantly, phosphorylation of the DA downstream effector, DA and cAMP-regulated phosphoprotein of 32 kDa (DARPP-32), was only significantly reduced in Group 2 NF1-NPCs (FIG. 15C). Together, these findings establish a strong relationship between neurofibromin expression and DA homeostasis/signaling (FIGS. 15B and 15D).

In the Examples provided herein, a combination of NF1-patient primary fibroblasts as well as derivative iPSCs and NPCs were employed to explore the mechanistic relationship between the germline NF1 gene mutation and neurofibromin expression/function. The deployment of these unique NF1-patient bio specimens along with Nf1 genetically-engineered mouse strains provided complementary evidence relevant to disease heterogeneity, biomarker implementation and risk assessment in this common neurogenetic condition. Germline NF1 gene mutations result in dramatically different effects on neurofibromin expression in primary cells from individuals with NF1 One group of individuals with NF1 harbored >70% reductions in neurofibromin expression after a single germline mutation regardless of the cell lineage. The clinical importance of differential neurofibromin expression caused by a single germline mutation is especially germane to the interpretation of Nf1 GEM studies that focus on phenotypes dictated by NF1 gene heterozygosity, such as behavior and learning. All NF1-patient fibroblasts, iPSCs and NPCs exhibited high levels of RAS activity, regardless of the level of neurofibromin expression. This indicates that the RAS-GAP activity of neurofibromin is it is comparably impaired in all individuals with NF1, irrespective of the nature or location of the germline NF1 gene mutation, and is thus highly sensitive to NF1 gene mutation. Low hippocampal DA levels and downstream signaling, as measured by reduced DARPP-32 phosphorylation, are associated with impaired spatial learning in mice.

Disclosed herein are methods for diagnosing cognitive and behavioral disorders in subjects with neurofibromatosis type 1 (NF1). In particular methods are disclosed for assessing neurofibromin expression, dopamine expression and phosphorylation of DARPP-32. Reduction in expression of these biomarkers results in impaired memory and behavioral disorders. Since cognitive problems in neurological disorders can be difficult to identify, particularly in non-verbal or young children, predictive molecular biomarkers including neurofibromin, dopamine and phosphorylated DARPP-32 provide especially useful for the early diagnosis of these problems and the appropriate treatment of affected individuals.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for detecting neurofibromin expression pattern in a subject, the method comprising: obtaining a sample from a subject, the sample selected from the group consisting of a white blood cell sample, a skin fibroblast sample, a non-cancerous cell, and combinations thereof; contacting the sample with a first antibody that specifically binds neurofibromin to obtain an expression level of neurofibromin in the subject; and detecting dopamine expression level in the sample from the subject by contacting the sample with a second antibody that specifically binds dopamine.

2. The method of claim 1 further comprising normalizing the expression level of neurofibromin to an expression level of α-tubulin detected in the sample.

3. The method of claim 1 further comprising detecting phosphorylation of dopamine and cAMP regulated neuronal phosphoprotein (DARPP-32) in the sample from the subject by contacting the sample with a third antibody that specifically binds phosphorylated DARPP-32.

4. The method of claim 3 further comprising normalizing the level of phosphorylated DARPP-32 with an expression level of non-phosphorylated DARPP-32 detected in the sample.

5. The method of claim 1 further comprising normalizing the level of dopamine with total protein level detected in the sample.

6. The method of claim 1 further comprising isolating and lysing the cells of the sample.

7. The method of claim 1, wherein the method comprises a Western Blot analysis.

8. The method of claim 1, wherein the subject is a vertebrate.

9. The method of claim 8, wherein the subject is selected from the group consisting of a human and a rodent.

10. The method of claim 9, wherein the subject is a human having or suspected of having Neurofibromatosis Type I.

11. The method of claim 10, wherein the subject has or is suspected of having one of a cognitive impairment and a behavioral disorder.

12. The method of claim 11, wherein the behavioral disorder is selected from the group consisting of attention deficit/hyperactivity disorder (ADHD), autism, and combinations thereof.

13. The method of claim 11, wherein the subject has a reduced amount of at least one of neurofibromin, dopamine and DARPP-32 as compared to a subject that does not have Neurofibromatosis Type I.

14. The method of claim 1 further comprising detecting at least one of neurofibromin, dopamine, and DARPP-32 in an additional tissue obtained from the subject.

15. The method of claim 14 wherein the additional tissue is selected from the group consisting of brain, hippocampi, and a combination thereof.

16. A method of quantifying a level of neurofibromin, phosphorylated DARPP-32, and dopamine in a subject, the method comprising
(a) obtaining a sample from the subject, wherein the sample is selected from the group consisting of a white blood cell sample, a skin fibroblast sample, a brain sample, a hippocampus sample, and combinations thereof;
(b) isolating cells from the sample;
(c) lysing the cells isolated from the sample;
(d) extracting protein content from the cells; and
(e) detecting neurofibromin, phosphorylated DARPP-32, and dopamine in the extracted protein content by contacting the extracted protein content with an antibody that specifically binds neurofibromin, an antibody that specifically binds phosphorylated DARPP-32, and an antibody that specifically binds dopamine; and
(f) quantifying the level of at least one of neurofibromin, phosphorylated DARPP-32, and dopamine.

17. The method of claim 16 further comprising normalizing the level of at least one of neurofibromin with a-tubulin and phosphorylated DARPP-32 with non-phosphorylated DARPP-32 in the sample.

18. The method of claim 16 further comprising analyzing the level of at least one of neurofibromin, phosphorylated DARPP-32, and dopamine in the sample and a reference expression level of at least one of neurofibromin, phosphorylated DARPP-32, and dopamine.

19. The method of claim 16, wherein the subject has or is suspected of having at least one of neurofibromatosis type 1, a cognitive impairment, attention deficit/hyperactivity disorder (ADHD), autism, and combinations thereof.

* * * * *

SEQUENCE LISTING

```
<160> NUMBER OF SEQ ID NOS: 4

<210> SEQ ID NO 1
<211> LENGTH: 12444
<212> TYPE: DNA
<213> ORGANISM: Homo sapiens

<400> SEQUENCE: 1
aatctctagc tcgctcgcgc tccctctccc cgggccgtgg aaaggatccc acttccggtg     60
```

-continued

```
gggtgtcatg gcggcgtctc ggactgtgat ggctgtgggg agacggcgct agtggggaga       120
gcgaccaaga ggccccctcc cctcccgggg tcccttccc ctatcccct ccccccagcc         180 tccttgccaa cgccccttt ccctctcccc ctcccgctcg gcgctgaccc cccatcccca        240 ccccgtggg aacactggga gcctgcactc cacagaccct ctccttgcct cttccctcac        300
ctcagcctcc gctccccgcc ctcttcccgg cccagggcgc cggcccaccc ttccctccgc      360
cgccccccgg ccgcggggag gacatggccg cgcacaggcc ggtggaatgg gtccaggccg      420
tggtcagccg cttcgacgag cagcttccaa taaaaacagg acagcagaac acacatacca     480
aagtcagtac tgagcacaac aaggaatgtc taatcaatat ttccaaatac aagttttctt    540
tggttataag cggcctcact actattttaa agaatgttaa caatatgaga atatttggag   600
aagctgctga aaaaattta tatctctctc agttgattat attggataca ctggaaaaat    660
gtcttgctgg gcaaccaaag gacacaatga gattagatga aacgatgctg gtcaaacagt   720
tgctgccaga atctgccat tttcttcaca cctgtcgtga aggaaaccag catgcagctg    780
aacttcggaa ttctgcctct gggttttat tttctctcag ctgcaacaac ttcaatgcag    840 tcttagtcg catttctacc aggttacagg aattaactgt tgttcagaa gacaatgttg   900 atgttcatga tatagaattg ttacagtata tcaatgtgga ttgtgcaaaa ttaaaacgac   960
tcctgaagga aacagcattt aaatttaaag ccctaaagaa ggttgcgcag ttagcagtta  1020
taaatagcct ggaaaaggca ttttggaact gggtagaaaa ttatccagat gaattacaa   1080 aactgtacca gatcccacag actgatatgg ctgaatgtgc agaaaagcta tttgacttgg 1140
tggatggttt tgctgaaagc accaaacgta agcagcagt ttggccacta caaatcattc  1200
tccttatctt gtgtccagaa ataatccagg atatatccaa agacgtggtt gatgaaaaca 1260
acatgaataa gaagttattt ctggacagtc tacgaaaagc tcttgctggc catggaggaa 1320
gtaggcagct gacagaaagt gctgcaattg cctgtgtcaa actgtgtaaa gcaagtactt 1380
acatcaattg ggaagataac tctgtcattt tcctacttgt tcagtccatg gtggttgatc 1440
ttaagaacct gcttttaat ccaagtaagc cattctcaag aggcagtcag cctgcagatg  1500
tggatctaat gattgactgc cttgtttctt gctttcgtat aagccctcac aacaaccaac 1560
actttaagat ctgcctggct cagaattcac cttctacatt tcactatgtg ctggtaaatt 1620
cactccatcg aatcatcacc aattccgcat tggattggtg gcctaagatt gatgctgtgt 1680
attgtcactc ggttgaactt cgaaatatgt ttggtgaaac acttcataaa gcagtgcaag 1740
gttgtggagc acacccagca atacgaatgg caccgagtct tacatttaaa gaaaaagtaa 1800
caagccttaa atttaaagaa aaacctacag acctggagac aagaagctat aagtatcttc 1860
tcttgtccat ggtgaaacta attcatgcag atccaaagct cttgctttgt aatccaagaa 1920
aacaggggcc cgaaacccaa ggcagtacag cagaattaat tacagggctc gtccaactgg 1980
tccctcagtc acacatgcca gagattgctc aggaagcaat ggaggctctg ctggttcttc 2040
atcagttaga tagcattgat ttgtggaatc ctgatgctcc tgtagaaaca ttttgggaga 2100
ttagctcaca aatgcttttt tacatctgca agaaattaac tagtcatcaa atgcttagta 2160
gcacagaaat tctcaagtgg ttgcgggaaa tattgatctg caggaataaa tttcttctta 2220
aaaataagca ggcagataga agttcctgtc actttctcct tttttacggg gtaggatgtg 2280
atattccttc tagtggaaat accagtcaaa tgtccatgga tcatgaagaa ttactacgta 2340
ctcctggagc ctctctccgg aagggaaaag ggaactcctc tatggatagt gcagcaggat 2400
gcagcggaac ccccccgatt tgccgacaag cccagaccaa actagaagtg gccctgtaca 2460
```

```
tgtttctgtg gaaccctgac actgaagctg ttctggttgc catgtcctgt ttccgccacc   2520
tctgtgagga agcagatatc cggtgtgggg tggatgaagt gtcagtgcat aacctcttgc   2580
ccaactataa cacattcatg gagtttgcct ctgtcagcaa tatgatgtca acaggaagag   2640
cagcacttca gaaaagagtg atggcactgc tgaggcgcat tgagcatccc actgcaggaa   2700
acactgaggc ttgggaagat acacatgcaa aatgggaaca agcaacaaag ctaatcctta   2760
actatccaaa agccaaaatg gaagatgcc aggctgctga aagccttcac aagaccattg   2820
ttaagaggcg aatgtcccat gtgagtggag gaggatccat agatttgtct gacacagact   2880
ccctacagga atggatcaac atgactgct tcctttgtgc ccttggggga gtgtgcctcc   2940
agcagagaag caattctggc ctggcaacct atagcccacc catgggtcca gtcagtgaac   3000
gtaagggttc tatgatttca gtgatgtctt cagagggaaa cgcagataca cctgtcagca   3060
aatttatgga tcggctgttg tccttaatgg tgtgtaacca tgagaaagtg ggacttcaaa   3120 tacgaccaa tgttaaggat ctggtgggtc tagaattgag tcctgctctg tatccaatgc   3180
tatttaacaa attgaagaat accatcagca agttttttga ctcccaagga caggttttat   3240
tgactgatac caatactcaa tttgtagaac aaaccatagc tataatgaag aacttgctag   3300
ataatcatac tgaaggcagc tctgaacatc tagggcaagc tagcattgaa acaatgatgt   3360
taaatctggt caggtatgtt cgtgtgcttg ggatatggt ccatgcaatt caaataaaaa   3420
cgaaactgtg tcaattagtt gaagtaatga tggcaaggag agatgacctc tcattttgcc   3480
aagagatgaa atttaggaat aagatggtag aatacctgac agactgggtt atgggaacat   3540
caaaccaagc agcagatgat gatgtaaaat gtcttacaag agatttggac caggcaagca   3600
tggaagcagt agtttcactt ctagctggtc tccctctgca gcctgaagaa ggagatggtg   3660
tggaattgat ggaagccaaa tcacagttat ttcttaaata cttcacatta tttatgaacc   3720
ttttgaatga ctgcagtgaa gttgaagatg aaagtgcgca aacaggtggc aggaaacgtg   3780
gcatgtctcg gaggctggca tcactgaggc actgtacggt ccttgcaatg tcaaacttac   3840
tcaatgccaa cgtagacagt ggtctcatgc actccatagg cttaggttac cacaaggatc   3900
tccagacaag agctacattt atggaagttc tgacaaaaat ccttcaacaa ggcacagaat   3960
ttgacacact tgcagaaaca gtattggctg atcggtttga gagattggtg gaactggtca   4020
caatgatggg tgatcaagga gaactcccta tagcgatggc tctggccaat gtggttcctt   4080
gttctcagtg ggatgaacta gctcgagttc tggttactct gtttgattct cggcatttac   4140
tctaccaact gctctggaac atgttttcta agaagtagaa attggcagac tccatgcaga   4200
ctctcttccg aggcaacagc ttggccagta aataatgac attctgtttc aaggtatatg   4260
gtgctaccta tctacaaaaa ctcctggatc ctttattacg aattgtgatc acatcctctg   4320
attggcaaca tgttagcttt gaagtggatc ctaccaggtt agaaccatca gagagccttg   4380
aggaaaacca gcggaacctc cttcagatga ctgaaaagtt cttccatgcc atcatcagtt   4440
cctcctcaga attcccccct caacttcgaa gtgtgtgcca ctgtttatac caggcaactt   4500
gccactccct actgaataaa gctacagtaa aagaaaaaa ggaaaacaaa aaatcagtgg   4560
ttagccagcg tttccctcag aacagcatcg gtgcagtagg aagtgccatg ttcctcgat   4620 ttatcaatcc tgccattgtc tcaccgtatg aagcagggat tttagataaa agccaccac   4680 ctagaatcga aaggggcttg aagttaatgt caaagatact tcagagtatt gccaatcatg   4740
ttctcttcac aaaagaagaa catatgcggc ctttcaatga ttttgtgaaa agcaactttg   4800
```

```
atgcagcacg caggttttc cttgatatag catctgattg tcctacaagt gatgcagtaa    4860
atcatagtct ttccttcata agtgacggca atgtgcttgc tttacatcgt ctactctgga    4920
acaatcagga gaaaattggg cagtatcttt ccagcaacag ggatcataaa gctgttggaa    4980
gacgaccttt tgataagatg gcaacacttc ttgcatacct gggtcctcca gagcacaaac    5040
ctgtggcaga tacacactgg tccagcctta accttaccag ttcaaagttt gaggaattta    5100
tgactaggca tcaggtacat gaaaaagaag aattcaaggc tttgaaaacg ttaagtattt    5160
tctaccaagc tgggacttcc aaagctggga atcctatttt ttattatgtt gcacggaggt    5220
tcaaaactgg tcaaatcaat ggtgatttgc tgatatacca tgtcttactg actttaaagc    5280
catattatgc aaagccatat gaaattgtag tggaccttac ccataccggg cctagcaatc    5340
gctttaaaac agactttctc tctaagtggt ttgttgtttt tcctggcttt gcttacgaca    5400
acgtctccgc agtctatatc tataactgta actcctgggt cagggagtac accaagtatc    5460
atgagcggct gctgactggc ctcaaaggta gcaaaaggct tgttttcata gactgtcctg    5520
ggaaactggc tgagcacata gagcatgaac aacagaaact acctgctgcc accttggctt    5580
tagaagagga cctgaaggta ttccacaatg ctctcaagct agctcacaaa gacaccaaag    5640
tttctattaa agttggttct actgctgtcc aagtaacttc agcagagcga acaaaagtcc    5700
tagggcaatc agtctttcta aatgacattt attatgcttc ggaaattgaa gaaatctgcc    5760
tagtagatga gaaccagttc accttaacca ttgcaaacca gggcacgccg ctcaccttca    5820
tgcaccagga gtgtgaagcc attgtccagt ctatcattca tatccggacc cgctgggaac    5880
tgtcacagcc cgactctatc ccccaacaca ccaagattcg gccaaaagat gtccctggga    5940
cactgctcaa tatcgcatta cttaattag gcagttctga cccgagttta cggtcagctg    6000
cctataatct tctgtgtgcc ttaacttgta cctttaattt aaaaatcgag ggccagttac    6060
tagagacatc aggtttatgt atccctgcca acaacaccct ctttattgtc tctattagta    6120
agacactggc agccaatgag ccacacctca cgttagaatt tttggaagag tgtatttctg    6180
gatttagcaa atctagtatt gaattgaaac ccttgtttt ggaatacatg actccatggc    6240
tgtcaaatct agttcgtttt tgcaagcata atgatgatgc caaacgacaa agagttactg    6300
ctattcttga caagctgata acaatgacca tcaatgaaaa acagatgtac ccatctattc    6360
aagcaaaaat atggggaagc cttgggcaga ttacagatct gcttgatgtt gtactagaca    6420
gtttcatcaa aaccagtgca acaggtggct tgggatcaat aaaagctgag gtgatggcag    6480
atactgctgt agctttggct tctggaaatg tgaaattggt ttcaagcaag gttattggaa    6540
ggatgtgcaa ataattgac aagacatgct tatctccaac tcctacttta gaacaacatc    6600
ttatgtggga tgatattgct attttagcac gctacatgct gatgctgtcc ttcaacaatt    6660
cccttgatgt ggcagctcat cttccctacc tcttccacgt tgttactttc ttagtagcca    6720
caggtccgct ctcccttaga gcttccacac atggactggt cattaatatc attcactctc    6780
tgtgtacttg ttcacagctt cattttagtg aagagaccaa gcaagttttg agactcagtc    6840
tgacagagtt ctcattaccc aaattttact tgctgtttgg cattagcaaa gtcaagtcag    6900
ctgctgtcat tgccttccgt tccagttacc gggacaggtc attctctcct ggctcctatg    6960
agagagagac ttttgctttg acatccttgg aaacagtcac agaagctttg ttggagatca    7020
tggaggcatg catgagagat attccaacgt gcaagtggct ggaccagtgg acagaactag    7080
ctcaaagatt tgcattccaa tataatccat ccctgcaacc aagagctctt gttgtctttg    7140
ggtgtattag caaacgagtg tctcatgggc agataaagca gataatccgt attcttagca    7200
```

```
aggcacttga gagttgctta aaaggacctg acacttacaa cagtcaagtt ctgatagaag    7260
ctacagtaat agcactaacc aaattacagc cacttcttaa taaggactcg cctctgcaca    7320
aagccctctt ttgggtagct gtggctgtgc tgcagcttga tgaggtcaac ttgtattcag    7380
caggtaccgc acttcttgaa caaacctgc atactttaga tagtctccgt atattcaatg     7440
acaagagtcc agaggaagta tttatggcaa tccggaatcc tctggagtgg cactgcaagc    7500
aaatggatca ttttgttgga ctcaatttca actctaactt taactttgca ttggttggac    7560 acctttaaa agggtacagg catccttcac ctgctattgt tgcaagaaca gtcagaattt     7620
tacatacact actaactctg gttaacaaac acagaaattg tgacaaattt gaagtgaata    7680
cacagagcgt ggcctactta gcagctttac ttacagtgtc tgaagaagtt cgaagtcgct    7740
gcagcctaaa acatagaaag tcacttcttc ttactgatat ttcaatggaa aatgttccta    7800
tggatacata tcccattcat catggtgacc cttcctatag gacactaaag gagactcagc    7860
catggtcctc tcccaaaggt tctgaaggat accttgcagc cacctatcca actgtcggcc    7920
agaccagtcc ccgagccagg aaatccatga gcctggacat ggggcaacct tctcaggcca    7980
acactaagaa gttgcttgga acaaggaaaa gttttgatca cttgatatca gacacaaagg    8040
ctcctaaaag gcaagaaatg gaatcaggga tcacaacacc ccccaaaatg aggagagtag    8100
cagaaactga ttatgaaatg gaaactcaga ggatttcctc atcacaacag cacccacatt    8160
tacgtaaagt ttcagtgtct gaatcaaatg ttctcttgga tgaagaagta cttactgatc    8220
cgaagatcca ggcgctgctt cttactgttc tagctacact ggtaaaatat accacagatg    8280
agtttgatca acgaattctt tatgaatact tagcagaggc cagtgttgtg tttcccaaag    8340
tctttcctgt tgtgcataat ttgttggact ctaagatcaa caccctgtta tcattgtgcc    8400
aagatccaaa tttgttaaat ccaatccatg gaattgtgca gagtgtggtg taccatgaag    8460
aatccccacc acaataccaa acatcttacc tgcaaagttt tggttttaat ggcttgtggc    8520
ggtttgcagg accgttttca aagcaaacac aaattccaga ctatgctgag cttattgtta    8580 agttcttga tgccttgatt gacacgtacc tgcctggaat tgatgaagaa accagtgaag     8640
aatccctcct gactcccaca tctccttacc ctcctgcact gcagagccag cttagtatca    8700
ctgccaacct taacctttct aattccatga cctcacttgc aacttccag cattccccag     8760 gaatcgacaa ggagaacgtt gaactctccc ctaccactgg ccactgtaac agtggacgaa    8820
ctcgccacgg atccgcaagc caagtgcaga agcaaagaag cgctggcagt ttcaaacgta    8880
atagcattaa gaagatcgtg tgaagcttgc ttgctttctt ttttaaaatc aacttaacat    8940
gggctcttca ctagtgaccc cttccctgtc cttgcccttt ccccccatgt tgtaatgctg    9000
cacttcctgt tttataatga acccatccgg tttgccatgt tgccagatga tcaactcttc    9060
gaagccttgc ctaaatttaa tgctgccttt tctttaactt ttttttcttct acttttggcg    9120 tgtatctggt atatgtaagt gttcagaaca actgcaaaga aagtgggagg tcaggaaact    9180
tttaactgag aaatctcaat tgtaagagag gatgaattct tgaatactgc tactactggc    9240
cagtgatgaa agccatttgc acagagctct gccttctgtg gttttccctt cttcatccta    9300
cagagtaaag tgttagtcct atttatacat ttttcaagat acaagtttat gagagaaata    9360
gtattataac cccagtatgt ttaatctttt agctgtggac ttttttttta accgtacaaa    9420
actgaaagaa cctagagggt caagcctcag tgacttgaca ccataaagcc acagacaagg    9480
tacttggggg ggagggcagg gaaatttcat atttttatagt ggattcttaa gaaatactaa    9540
```

```
cacttgagta ttagcaataa ttacaggaaa ataagtgcga ccacatatat cttaacatta    9600
ctgaattaaa actatggctt ctaagtcctt atccaaactc agtcatccaa actagtttat    9660
ttttttctcc agttgattat cttttaattt ttaattttgc taaaggtggt ttttttgtgt    9720 tttgttttt  gtaaaccaaa actatactaa gtatagtaat tatatatata tatatatttt    9780
ttcccctccc cctcttcttt cctaactaat tctgagcagg gtaatcagtg aacaaagtgt    9840
tgaaaattgt tcccagaagg taattttcat agatgtttgc attagctcca tagcaaaatg    9900
gaatggtacg tgacatttag ggtagctgat attttattt tgttaaataa tttccaagaa    9960
tagagtatgg tgtatattat aaatttcttt gataagatgt attttgaatg tcttttaatc   10020
ttcctcctcc tctccaaaaa aatcagaaac ctctttaaga aaacatgtag gttatatatg   10080
ctagaattgc atttaatcac tgtgaaaaga ctggtcagcc tgcattagta tgacagtagg   10140
ggggctgtta gaattgctgc tatactggtg gtatggatta tcatggcatt ggaattttca   10200
tagtaatgca gatccaattt cctttgtggta cctgcagttt acaaaataat ttgacttcag   10260
tgagcatatt ggtatctgga tgttccaatt tagaactaaa ccatatttat tacaaaaaga   10320
tattaatccc tctactccca ggttcccttt atatgttaag atataatggc tttgagggg    10380 gaaaaaataa acctagggga gagggagtt tcctgtagtg ctgtttcatt agaggatttc    10440
agtaaattaa attccacagc taattcaata aataatggta catttaagtg ttctgatttt   10500
aataatatat ttcacattta tccacacagt aacaatgtaa tatgttaatg taaataaaat   10560
tggttttgat actcagaaat aacaagaatt taatttttta aatttgttta cagtcctggg   10620
aaaagtaaga attatttgcc aaaataagag gaaagaaaac cttagtatta ttaatgagtt   10680
taccatagaa ttgttggaaa tactgaagac aggtgcaatt tactaaactt tgttttttaa   10740
actattgtag aggctgcatt agaagaaaat gtttataatg acagagcaac tatgactata   10800 taaaaagct  gaaattagaa ctgtgtttag aaatagatca gtaacccagt gccaaggatg   10860
ccaagctgcc accatggtct tggctctccc acaacccagt gtttctgggg taagtttcac   10920
agtttctagg ccctggaata gcaggcagtg taagcctttg ataactttag ttcgatgttt   10980
ttcttgtttt tgtttgttgg tttggtgcat atgatagtgg gtgttatgct attttgctct   11040
tcccatcaaa ataaagaaac ttccagaggt ttactgttaa aaatactgat atttccataa   11100
acgggtttac caagggtgta gtatttcata ccgcctgaaa tgatcagcat ggcacaaat    11160 caaaattcag ccgcctttga aatgcaaaaa tacctttgac tagtaagtac atcctaggag   11220
tttgaaaact taactaaggt ttaaaattta ccttgtttaa agaacttctg acttttgagg   11280
aaaatctagc tttccaagta actaaaatgt acatgagata aacctctcac cactatgtgt   11340
cccttgagaa atgcaacact ttttagtct tcatacttgt aatctataaa agaaattctg    11400
aagtttagac caagttgccc atttctgcgt aattgacata agttctgtta aaaatattat   11460
aagtaattcg tttcggtttg tagatgtttc ccctgacttg ttaaagagga aaccaggaac   11520
tcagtcatgt ttttgtcctg gataatctac ctgttatgcc agtactccca tccgaggggc   11580
atgcccttag ttgcccagat ggagatgcag ttcagtagat ttggggcaaa gtggctacag   11640
ctctgtcttc cattcactca cacctgttc atgactgagc caggtgccca ggacacatcc    11700
taaacagtca gcttctatcc tgtgtcctag ttggggagac agagtgccag ccagcaaccc   11760
tcccaggttt gtaggtttta gggttttca gttttgtttg ggttttttgt ttttgtttt    11820 tgtttctaca tccttccccg actcccaggc ataatgaggc atgtcttact caatgttatg   11880
caatggattt aggcaaaaat tcattcttag tgtcagccac acaatttttt ttaatgcagt   11940
```

```
atattcacct gtaaatagtt tgtgtaaaat ttgacaaaaa aagtatattt actatactgt    12000
aaatatatgt gatgatatat tgtattattt tgctttttg taaagcagtt agttgctgca    12060
catggataac aacaaaaatt tgattattct cgtgttagta ttgttaactt cttttgcga    12120 ctgcgttaca tcatttaaag aaaatgctgt gtattgtaaa cttaaattgt atatgataac   12180
ttactgtcct ttccatccgg gcctaaactt tggcagttcc tttgtctaca accttgttaa   12240
tactgtaaac agttgtacgc cagcaggaaa aatactgccc aacagacaaa atcgatcatt   12300 gtagggaaa atcatagaaa tccatttcag atctttattg ttcctcaccc cattttcctc    12360
cttgtgtatg tacttccccc accccctttt tttaagtaa aatgtaaatt caatctgctc    12420
taagaaaaaa aaaaaaaaaa aaaa                                          12444
```

<210> SEQ ID NO 2
<211> LENGTH: 2839
<212> TYPE: PRT
<213> ORGANISM: Homo sapiens

<400> SEQUENCE: 2

```
Met Ala Ala His Arg Pro Val Glu Trp Val Gln Ala Val Val Ser Arg
1               5                   10                  15

Phe Asp Glu Gln Leu Pro Ile Lys Thr Gly Gln Gln Asn Thr His Thr
                20                  25                  30

Lys Val Ser Thr Glu His Asn Lys Glu Cys Leu Ile Asn Ile Ser Lys
            35                  40                  45

Tyr Lys Phe Ser Leu Val Ile Ser Gly Leu Thr Thr Ile Leu Lys Asn
50                  55                  60

Val Asn Asn Met Arg Ile Phe Gly Glu Ala Ala Glu Lys Asn Leu Tyr
65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
            100                 105                 110

Leu Leu Pro Glu Ile Cys His Phe Leu His Thr Cys Arg Glu Gly Asn
        115                 120                 125

Gln His Ala Ala Glu Leu Arg Asn Ser Ala Ser Gly Val Leu Phe Ser
    130                 135                 140

Leu Ser Cys Asn Asn Phe Asn Ala Val Phe Ser Arg Ile Ser Thr Arg
145                 150                 155                 160

Leu Gln Glu Leu Thr Val Cys Ser Glu Asp Asn Val Asp Val His Asp
                165                 170                 175

Ile Glu Leu Leu Gln Tyr Ile Asn Val Asp Cys Ala Lys Leu Lys Arg
            180                 185                 190

Leu Leu Lys Glu Thr Ala Phe Lys Phe Lys Ala Leu Lys Lys Val Ala
        195                 200                 205

Gln Leu Ala Val Ile Asn Ser Leu Glu Lys Ala Phe Trp Asn Trp Val
    210                 215                 220

Glu Asn Tyr Pro Asp Glu Phe Thr Lys Leu Tyr Gln Ile Pro Gln Thr
225                 230                 235                 240

Asp Met Ala Glu Cys Ala Glu Lys Leu Phe Asp Leu Val Asp Gly Phe
                245                 250                 255

Ala Glu Ser Thr Lys Arg Lys Ala Ala Val Trp Pro Leu Gln Ile Ile
            260                 265                 270

Leu Leu Ile Leu Cys Pro Glu Ile Ile Gln Asp Ile Ser Lys Asp Val
```

```
            275                 280                 285
Val Asp Glu Asn Asn Met Asn Lys Lys Leu Phe Leu Asp Ser Leu Arg
290                 295                 300

Lys Ala Leu Ala Gly His Gly Gly Ser Arg Gln Leu Thr Glu Ser Ala
305                 310                 315                 320

Ala Ile Ala Cys Val Lys Leu Cys Lys Ala Ser Thr Tyr Ile Asn Trp
                325                 330                 335

Glu Asp Asn Ser Val Ile Phe Leu Leu Val Gln Ser Met Val Val Asp
            340                 345                 350

Leu Lys Asn Leu Leu Phe Asn Pro Ser Lys Pro Phe Ser Arg Gly Ser
        355                 360                 365

Gln Pro Ala Asp Val Asp Leu Met Ile Asp Cys Leu Val Ser Cys Phe
370                 375                 380

Arg Ile Ser Pro His Asn Asn Gln His Phe Lys Ile Cys Leu Ala Gln
385                 390                 395                 400

Asn Ser Pro Ser Thr Phe His Tyr Val Leu Val Asn Ser Leu His Arg
                405                 410                 415

Ile Ile Thr Asn Ser Ala Leu Asp Trp Trp Pro Lys Ile Asp Ala Val
            420                 425                 430

Tyr Cys His Ser Val Glu Leu Arg Asn Met Phe Gly Glu Thr Leu His
        435                 440                 445

Lys Ala Val Gln Gly Cys Gly Ala His Pro Ala Ile Arg Met Ala Pro
450                 455                 460

Ser Leu Thr Phe Lys Glu Lys Val Thr Ser Leu Lys Phe Lys Glu Lys
465                 470                 475                 480

Pro Thr Asp Leu Glu Thr Arg Ser Tyr Lys Tyr Leu Leu Leu Ser Met
                485                 490                 495

Val Lys Leu Ile His Ala Asp Pro Lys Leu Leu Leu Cys Asn Pro Arg
            500                 505                 510

Lys Gln Gly Pro Glu Thr Gln Gly Ser Thr Ala Glu Leu Ile Thr Gly
        515                 520                 525

Leu Val Gln Leu Val Pro Gln Ser His Met Pro Glu Ile Ala Gln Glu
530                 535                 540

Ala Met Glu Ala Leu Leu Val Leu His Gln Leu Asp Ser Ile Asp Leu
545                 550                 555                 560

Trp Asn Pro Asp Ala Pro Val Glu Thr Phe Trp Glu Ile Ser Ser Gln
                565                 570                 575

Met Leu Phe Tyr Ile Cys Lys Lys Leu Thr Ser His Gln Met Leu Ser
            580                 585                 590

Ser Thr Glu Ile Leu Lys Trp Leu Arg Glu Ile Leu Ile Cys Arg Asn
        595                 600                 605

Lys Phe Leu Leu Lys Asn Lys Gln Ala Asp Arg Ser Ser Cys His Phe
610                 615                 620

Leu Leu Phe Tyr Gly Val Gly Cys Asp Ile Pro Ser Ser Gly Asn Thr
625                 630                 635                 640

Ser Gln Met Ser Met Asp His Glu Glu Leu Leu Arg Thr Pro Gly Ala
                645                 650                 655

Ser Leu Arg Lys Gly Lys Gly Asn Ser Ser Met Asp Ser Ala Ala Gly
            660                 665                 670

Cys Ser Gly Thr Pro Pro Ile Cys Arg Gln Ala Gln Thr Lys Leu Glu
        675                 680                 685

Val Ala Leu Tyr Met Phe Leu Trp Asn Pro Asp Thr Glu Ala Val Leu
690                 695                 700
```

```
Val Ala Met Ser Cys Phe Arg His Leu Cys Glu Glu Ala Asp Ile Arg
705                 710                 715                 720

Cys Gly Val Asp Glu Val Ser Val His Asn Leu Leu Pro Asn Tyr Asn
                725                 730                 735

Thr Phe Met Glu Phe Ala Ser Val Ser Asn Met Met Ser Thr Gly Arg
                740                 745                 750

Ala Ala Leu Gln Lys Arg Val Met Ala Leu Leu Arg Arg Ile Glu His
                755                 760                 765

Pro Thr Ala Gly Asn Thr Glu Ala Trp Glu Asp Thr His Ala Lys Trp
770                 775                 780

Glu Gln Ala Thr Lys Leu Ile Leu Asn Tyr Pro Lys Ala Lys Met Glu
785                 790                 795                 800

Asp Gly Gln Ala Ala Glu Ser Leu His Lys Thr Ile Val Lys Arg Arg
                805                 810                 815

Met Ser His Val Ser Gly Gly Ser Ile Asp Leu Ser Asp Thr Asp
                820                 825                 830

Ser Leu Gln Glu Trp Ile Asn Met Thr Gly Phe Leu Cys Ala Leu Gly
                835                 840                 845

Gly Val Cys Leu Gln Gln Arg Ser Asn Ser Gly Leu Ala Thr Tyr Ser
                850                 855                 860

Pro Pro Met Gly Pro Val Ser Glu Arg Lys Gly Ser Met Ile Ser Val
865                 870                 875                 880

Met Ser Ser Glu Gly Asn Ala Asp Thr Pro Val Ser Lys Phe Met Asp
                885                 890                 895

Arg Leu Leu Ser Leu Met Val Cys Asn His Glu Lys Val Gly Leu Gln
                900                 905                 910

Ile Arg Thr Asn Val Lys Asp Leu Val Gly Leu Glu Leu Ser Pro Ala
                915                 920                 925

Leu Tyr Pro Met Leu Phe Asn Lys Leu Lys Asn Thr Ile Ser Lys Phe
                930                 935                 940

Phe Asp Ser Gln Gly Gln Val Leu Leu Thr Asp Thr Asn Thr Gln Phe
945                 950                 955                 960

Val Glu Gln Thr Ile Ala Ile Met Lys Asn Leu Leu Asp Asn His Thr
                965                 970                 975

Glu Gly Ser Ser Glu His Leu Gly Gln Ala Ser Ile Glu Thr Met Met
                980                 985                 990

Leu Asn Leu Val Arg Tyr Val Arg  Val Leu Gly Asn Met  Val His Ala
                995                 1000                1005

Ile Gln  Ile Lys Thr Lys Leu  Cys Gln Leu Val Glu  Val Met Met
    1010                1015                1020

Ala Arg  Arg Asp Asp Leu Ser  Phe Cys Gln Glu Met  Lys Phe Arg
    1025                1030                1035

Asn Lys  Met Val Glu Tyr Leu  Thr Asp Trp Val Met  Gly Thr Ser
    1040                1045                1050

Asn Gln  Ala Ala Asp Asp  Val Lys Cys Leu Thr  Arg Asp Leu
    1055                1060                1065

Asp Gln  Ala Ser Met Glu Ala  Val Val Ser Leu Leu  Ala Gly Leu
    1070                1075                1080

Pro Leu  Gln Pro Glu Glu Gly  Asp Gly Val Glu Leu  Met Glu Ala
    1085                1090                1095

Lys Ser  Gln Leu Phe Leu Lys  Tyr Phe Thr Leu Phe  Met Asn Leu
    1100                1105                1110
```

-continued

```
Leu Asn Asp Cys Ser Glu Val Glu Asp Glu Ser Ala Gln Thr Gly
    1115                1120                1125

Gly Arg Lys Arg Gly Met Ser Arg Arg Leu Ala Ser Leu Arg His
    1130                1135                1140

Cys Thr Val Leu Ala Met Ser Asn Leu Leu Asn Ala Asn Val Asp
    1145                1150                1155

Ser Gly Leu Met His Ser Ile Gly Leu Gly Tyr His Lys Asp Leu
    1160                1165                1170

Gln Thr Arg Ala Thr Phe Met Glu Val Leu Thr Lys Ile Leu Gln
    1175                1180                1185

Gln Gly Thr Glu Phe Asp Thr Leu Ala Glu Thr Val Leu Ala Asp
    1190                1195                1200

Arg Phe Glu Arg Leu Val Glu Leu Val Thr Met Met Gly Asp Gln
    1205                1210                1215

Gly Glu Leu Pro Ile Ala Met Ala Leu Ala Asn Val Val Pro Cys
    1220                1225                1230

Ser Gln Trp Asp Glu Leu Ala Arg Val Leu Val Thr Leu Phe Asp
    1235                1240                1245

Ser Arg His Leu Leu Tyr Gln Leu Leu Trp Asn Met Phe Ser Lys
    1250                1255                1260

Glu Val Glu Leu Ala Asp Ser Met Gln Thr Leu Phe Arg Gly Asn
    1265                1270                1275

Ser Leu Ala Ser Lys Ile Met Thr Phe Cys Phe Lys Val Tyr Gly
    1280                1285                1290

Ala Thr Tyr Leu Gln Lys Leu Leu Asp Pro Leu Leu Arg Ile Val
    1295                1300                1305

Ile Thr Ser Ser Asp Trp Gln His Val Ser Phe Glu Val Asp Pro
    1310                1315                1320

Thr Arg Leu Glu Pro Ser Glu Ser Leu Glu Glu Asn Gln Arg Asn
    1325                1330                1335

Leu Leu Gln Met Thr Glu Lys Phe Phe His Ala Ile Ile Ser Ser
    1340                1345                1350

Ser Ser Glu Phe Pro Pro Gln Leu Arg Ser Val Cys His Cys Leu
    1355                1360                1365

Tyr Gln Ala Thr Cys His Ser Leu Leu Asn Lys Ala Thr Val Lys
    1370                1375                1380

Glu Lys Lys Glu Asn Lys Lys Ser Val Val Ser Gln Arg Phe Pro
    1385                1390                1395

Gln Asn Ser Ile Gly Ala Val Gly Ser Ala Met Phe Leu Arg Phe
    1400                1405                1410

Ile Asn Pro Ala Ile Val Ser Pro Tyr Glu Ala Gly Ile Leu Asp
    1415                1420                1425

Lys Lys Pro Pro Arg Ile Glu Arg Gly Leu Lys Leu Met Ser
    1430                1435                1440

Lys Ile Leu Gln Ser Ile Ala Asn His Val Leu Phe Thr Lys Glu
    1445                1450                1455

Glu His Met Arg Pro Phe Asn Asp Phe Val Lys Ser Asn Phe Asp
    1460                1465                1470

Ala Ala Arg Arg Phe Phe Leu Asp Ile Ala Ser Asp Cys Pro Thr
    1475                1480                1485

Ser Asp Ala Val Asn His Ser Leu Ser Phe Ile Ser Asp Gly Asn
    1490                1495                1500

Val Leu Ala Leu His Arg Leu Leu Trp Asn Asn Gln Glu Lys Ile
```

```
                1505                 1510                1515

Gly Gln Tyr Leu Ser Ser Asn Arg Asp His Lys Ala Val Gly Arg
    1520                1525                1530

Arg Pro Phe Asp Lys Met Ala Thr Leu Leu Ala Tyr Leu Gly Pro
    1535                1540                1545

Pro Glu His Lys Pro Val Ala Asp Thr His Trp Ser Ser Leu Asn
    1550                1555                1560

Leu Thr Ser Ser Lys Phe Glu Glu Phe Met Thr Arg His Gln Val
    1565                1570                1575

His Glu Lys Glu Glu Phe Lys Ala Leu Lys Thr Leu Ser Ile Phe
    1580                1585                1590

Tyr Gln Ala Gly Thr Ser Lys Ala Gly Asn Pro Ile Phe Tyr Tyr
    1595                1600                1605

Val Ala Arg Arg Phe Lys Thr Gly Gln Ile Asn Gly Asp Leu Leu
    1610                1615                1620

Ile Tyr His Val Leu Leu Thr Leu Lys Pro Tyr Tyr Ala Lys Pro
    1625                1630                1635

Tyr Glu Ile Val Val Asp Leu Thr His Thr Gly Pro Ser Asn Arg
    1640                1645                1650

Phe Lys Thr Asp Phe Leu Ser Lys Trp Phe Val Val Phe Pro Gly
    1655                1660                1665

Phe Ala Tyr Asp Asn Val Ser Ala Val Tyr Ile Tyr Asn Cys Asn
    1670                1675                1680

Ser Trp Val Arg Glu Tyr Thr Lys Tyr His Glu Arg Leu Leu Thr
    1685                1690                1695

Gly Leu Lys Gly Ser Lys Arg Leu Val Phe Ile Asp Cys Pro Gly
    1700                1705                1710

Lys Leu Ala Glu His Ile Glu His Glu Gln Gln Lys Leu Pro Ala
    1715                1720                1725

Ala Thr Leu Ala Leu Glu Glu Asp Leu Lys Val Phe His Asn Ala
    1730                1735                1740

Leu Lys Leu Ala His Lys Asp Thr Lys Val Ser Ile Lys Val Gly
    1745                1750                1755

Ser Thr Ala Val Gln Val Thr Ser Ala Glu Arg Thr Lys Val Leu
    1760                1765                1770

Gly Gln Ser Val Phe Leu Asn Asp Ile Tyr Tyr Ala Ser Glu Ile
    1775                1780                1785

Glu Glu Ile Cys Leu Val Asp Glu Asn Gln Phe Thr Leu Thr Ile
    1790                1795                1800

Ala Asn Gln Gly Thr Pro Leu Thr Phe Met His Gln Glu Cys Glu
    1805                1810                1815

Ala Ile Val Gln Ser Ile Ile His Ile Arg Thr Arg Trp Glu Leu
    1820                1825                1830

Ser Gln Pro Asp Ser Ile Pro Gln His Thr Lys Ile Arg Pro Lys
    1835                1840                1845

Asp Val Pro Gly Thr Leu Leu Asn Ile Ala Leu Leu Asn Leu Gly
    1850                1855                1860

Ser Ser Asp Pro Ser Leu Arg Ser Ala Ala Tyr Asn Leu Leu Cys
    1865                1870                1875

Ala Leu Thr Cys Thr Phe Asn Leu Lys Ile Glu Gly Gln Leu Leu
    1880                1885                1890

Glu Thr Ser Gly Leu Cys Ile Pro Ala Asn Asn Thr Leu Phe Ile
    1895                1900                1905
```

```
Val Ser Ile Ser Lys Thr Leu Ala Ala Asn Glu Pro His Leu Thr
    1910            1915                1920

Leu Glu Phe Leu Glu Glu Cys Ile Ser Gly Phe Ser Lys Ser Ser
    1925            1930                1935

Ile Glu Leu Lys His Leu Cys Leu Glu Tyr Met Thr Pro Trp Leu
    1940            1945                1950

Ser Asn Leu Val Arg Phe Cys Lys His Asn Asp Asp Ala Lys Arg
    1955            1960                1965

Gln Arg Val Thr Ala Ile Leu Asp Lys Leu Ile Thr Met Thr Ile
    1970            1975                1980

Asn Glu Lys Gln Met Tyr Pro Ser Ile Gln Ala Lys Ile Trp Gly
    1985            1990                1995

Ser Leu Gly Gln Ile Thr Asp Leu Leu Asp Val Val Leu Asp Ser
    2000            2005                2010

Phe Ile Lys Thr Ser Ala Thr Gly Gly Leu Gly Ser Ile Lys Ala
    2015            2020                2025

Glu Val Met Ala Asp Thr Ala Val Ala Leu Ala Ser Gly Asn Val
    2030            2035                2040

Lys Leu Val Ser Ser Lys Val Ile Gly Arg Met Cys Lys Ile Ile
    2045            2050                2055

Asp Lys Thr Cys Leu Ser Pro Thr Pro Thr Leu Glu Gln His Leu
    2060            2065                2070

Met Trp Asp Asp Ile Ala Ile Leu Ala Arg Tyr Met Leu Met Leu
    2075            2080                2085

Ser Phe Asn Asn Ser Leu Asp Val Ala Ala His Leu Pro Tyr Leu
    2090            2095                2100

Phe His Val Val Thr Phe Leu Val Ala Thr Gly Pro Leu Ser Leu
    2105            2110                2115

Arg Ala Ser Thr His Gly Leu Val Ile Asn Ile Ile His Ser Leu
    2120            2125                2130

Cys Thr Cys Ser Gln Leu His Phe Ser Glu Glu Thr Lys Gln Val
    2135            2140                2145

Leu Arg Leu Ser Leu Thr Glu Phe Ser Leu Pro Lys Phe Tyr Leu
    2150            2155                2160

Leu Phe Gly Ile Ser Lys Val Lys Ser Ala Ala Val Ile Ala Phe
    2165            2170                2175

Arg Ser Ser Tyr Arg Asp Arg Ser Phe Ser Pro Gly Ser Tyr Glu
    2180            2185                2190

Arg Glu Thr Phe Ala Leu Thr Ser Leu Glu Thr Val Thr Glu Ala
    2195            2200                2205

Leu Leu Glu Ile Met Glu Ala Cys Met Arg Asp Ile Pro Thr Cys
    2210            2215                2220

Lys Trp Leu Asp Gln Trp Thr Glu Leu Ala Gln Arg Phe Ala Phe
    2225            2230                2235

Gln Tyr Asn Pro Ser Leu Gln Pro Arg Ala Leu Val Val Phe Gly
    2240            2245                2250

Cys Ile Ser Lys Arg Val Ser His Gly Gln Ile Lys Gln Ile Ile
    2255            2260                2265

Arg Ile Leu Ser Lys Ala Leu Glu Ser Cys Leu Lys Gly Pro Asp
    2270            2275                2280

Thr Tyr Asn Ser Gln Val Leu Ile Glu Ala Thr Val Ile Ala Leu
    2285            2290                2295
```

-continued

Thr Lys Leu Gln Pro Leu Leu Asn Lys Asp Ser Pro Leu His Lys
2300                2305                2310

Ala Leu Phe Trp Val Ala Val Ala Val Leu Gln Leu Asp Glu Val
2315                2320                2325

Asn Leu Tyr Ser Ala Gly Thr Ala Leu Leu Glu Gln Asn Leu His
2330                2335                2340

Thr Leu Asp Ser Leu Arg Ile Phe Asn Asp Lys Ser Pro Glu Glu
2345                2350                2355

Val Phe Met Ala Ile Arg Asn Pro Leu Glu Trp His Cys Lys Gln
2360                2365                2370

Met Asp His Phe Val Gly Leu Asn Phe Asn Ser Asn Phe Asn Phe
2375                2380                2385

Ala Leu Val Gly His Leu Leu Lys Gly Tyr Arg His Pro Ser Pro
2390                2395                2400

Ala Ile Val Ala Arg Thr Val Arg Ile Leu His Thr Leu Leu Thr
2405                2410                2415

Leu Val Asn Lys His Arg Asn Cys Asp Lys Phe Glu Val Asn Thr
2420                2425                2430

Gln Ser Val Ala Tyr Leu Ala Ala Leu Leu Thr Val Ser Glu Glu
2435                2440                2445

Val Arg Ser Arg Cys Ser Leu Lys His Arg Lys Ser Leu Leu Leu
2450                2455                2460

Thr Asp Ile Ser Met Glu Asn Val Pro Met Asp Thr Tyr Pro Ile
2465                2470                2475

His His Gly Asp Pro Ser Tyr Arg Thr Leu Lys Glu Thr Gln Pro
2480                2485                2490

Trp Ser Ser Pro Lys Gly Ser Glu Gly Tyr Leu Ala Ala Thr Tyr
2495                2500                2505

Pro Thr Val Gly Gln Thr Ser Pro Arg Ala Arg Lys Ser Met Ser
2510                2515                2520

Leu Asp Met Gly Gln Pro Ser Gln Ala Asn Thr Lys Lys Leu Leu
2525                2530                2535

Gly Thr Arg Lys Ser Phe Asp His Leu Ile Ser Asp Thr Lys Ala
2540                2545                2550

Pro Lys Arg Gln Glu Met Glu Ser Gly Ile Thr Thr Pro Pro Lys
2555                2560                2565

Met Arg Arg Val Ala Glu Thr Asp Tyr Glu Met Glu Thr Gln Arg
2570                2575                2580

Ile Ser Ser Ser Gln Gln His Pro His Leu Arg Lys Val Ser Val
2585                2590                2595

Ser Glu Ser Asn Val Leu Leu Asp Glu Glu Val Leu Thr Asp Pro
2600                2605                2610

Lys Ile Gln Ala Leu Leu Leu Thr Val Leu Ala Thr Leu Val Lys
2615                2620                2625

Tyr Thr Thr Asp Glu Phe Asp Gln Arg Ile Leu Tyr Glu Tyr Leu
2630                2635                2640

Ala Glu Ala Ser Val Val Phe Pro Lys Val Phe Pro Val Val His
2645                2650                2655

Asn Leu Leu Asp Ser Lys Ile Asn Thr Leu Leu Ser Leu Cys Gln
2660                2665                2670

Asp Pro Asn Leu Leu Asn Pro Ile His Gly Ile Val Gln Ser Val
2675                2680                2685

Val Tyr His Glu Glu Ser Pro Pro Gln Tyr Gln Thr Ser Tyr Leu

-continued

```
              2690                 2695                      2700
Gln Ser  Phe Gly Phe Asn Gly  Leu Trp Arg Phe Ala  Gly Pro Phe
         2705                 2710                 2715

Ser Lys  Gln Thr Gln Ile Pro  Asp Tyr Ala Glu Leu  Ile Val Lys
         2720                 2725                 2730

Phe Leu  Asp Ala Leu Ile Asp  Thr Tyr Leu Pro Gly  Ile Asp Glu
         2735                 2740                 2745

Glu Thr  Ser Glu Glu Ser Leu  Leu Thr Pro Thr Ser  Pro Tyr Pro
         2750                 2755                 2760

Pro Ala  Leu Gln Ser Gln Leu  Ser Ile Thr Ala Asn  Leu Asn Leu
         2765                 2770                 2775

Ser Asn  Ser Met Thr Ser Leu  Ala Thr Ser Gln His  Ser Pro Gly
         2780                 2785                 2790

Ile Asp  Lys Glu Asn Val Glu  Leu Ser Pro Thr Thr  Gly His Cys
         2795                 2800                 2805

Asn Ser  Gly Arg Thr Arg His  Gly Ser Ala Ser Gln  Val Gln Lys
         2810                 2815                 2820

Gln Arg  Ser Ala Gly Ser Phe  Lys Arg Asn Ser Ile  Lys Lys Ile
         2825                 2830                 2835

Val

<210> SEQ ID NO 3
<211> LENGTH: 11847
<212> TYPE: DNA
<213> ORGANISM: Mus musculus

<400> SEQUENCE: 3
ctcagccgct cggctcgccg ctgccctcac ctccgcgccg gccgcccgcc cgccctcagg      60
cgggccccgg acgccggccc tccaccgccc ccgggtcgcc gggaggacat ggccgcacac     120
aggccggtgg aatgggtcca ggccgtggtc agccgcttcg acgagcagct tccaataaag     180
acaggacagc agaacacaca taccaaagtc agcaccgagc acaacaagga gtgtctgatc     240
aacatttcca atacaagtt ttctctggtc atcagtgggc tcaccaccat cctaaagaat     300
gttaacaata tgaggatatt tggagaagct gctgaaaaaa atttgtatct ctctcagttg     360
atcatattgg atacactgga aaatgtcttg ctgggcaac caaaggacac aatgagatta     420
gatgagacaa tgctggtcaa acaattacta ccagaaatct gccattttct tcacacctgc     480
cgtgaaggaa accaacatgc agccgaactt cggaattctg cctctggggt tttatttct     540 ctcagctgca caacttcaa tgcagtcttt agtcgcattt ctacaaggtt acaggagttg     600
actgtctgtt cagaagataa tgttgatgtt cacgatatag aattgttaca gtatatcaat     660
gtggattgtg caaattaaa acgacttctg aaggaaacag catttaaatt taaagccctg     720
aagaaggttg cacagttggc agttataaat agcctagaaa aggcttttg gaactgggta     780 gaaaattatc cggatgaatt tacaaagcta taccaaattc cacagacaga tatggctgaa     840
tgtgcagaga agctgtttga cttggtggat ggttttgcag aaagcaccaa acgtaaagca     900
gcagtgtggc ccctacaaat cattctcctt atcttgtgtc cagaaataat ccaggacatc     960
tccaaggatg tggtggacga gagcaacata acaagaagc tgtttctgga cagtttacgg    1020
aaagcactcg ctggccatgg aggaagcagg cagctgactg agagtgctgc cattgcttgt    1080
gtcaagttgt gtaaagcaag tacttacatc aactgggaag ataattctgt catttttccta   1140 ctggttcagt ccatggtagt tgatcttaag aacctgcttt ttaatccaag taaaccattc    1200
```

-continued

```
tctagaggca gtcagcctgc agatgtggac ctcatgattg actgtcttgt ctcttgcttt      1260
cggataagcc ctcacaacaa ccaacacttt aagatctgcc tggctcagaa ttcaccttct      1320
acatttcact atgtgttggt aaactcactg caccgcatca tcaccaattc tgcgttggat      1380
tggtggccta agattgatgc tgtatattgt cactcagttg aacttcgcaa tatgtttggt      1440
gaaacacttc ataaagcagt gcaaggctgt ggagcgcacc cagcaatacg aatggcacca      1500
agtctcacct ttaaagaaaa ggtaacaagc cttaaattta agaaaagcc tacagaccta       1560
gagacaagga gctacaaatg tcttcttttg tccatggtga aactgattca tgcagaccca      1620
aagcttttgc tttgtaatcc aagaaaacag ggccctgaaa ctcagagcag tacagcagaa      1680
ctaattacag ggctcgtaca actggttcct cagtcacaca tgccagaggt cgctcaggag      1740
gctatggagg ctttgctggt ccttcatcag ttagatagca ttgatctctg gaatcctgac      1800
gctcctgtag agacattctg ggaaatcagc tcacaaatgc ttttttacat ctgcaagaaa      1860
ttaactagcc atcaaatgct tagtagcaca gaaattctca gtggttacg ggaaattctg       1920
atctgcagaa ataaatttct tcttaaaaat aagcaggcag atagaagctc ctgtcattct      1980
ctctaccttt atggagtagg atgtgaaatg tctgctactg gaaataccac tcagatgtca      2040
gttgatcatg atgagttcct gcgtgcctgt actcctggag catctctgcg gaaaggaaga      2100
gggaattcct ccatggatag cacagcaggg tgcagtggaa ccccacctat atgccgacaa      2160
gcccagacca agctagaagt ggccttatac atgtttctgt ggaatcctga cactgaagct      2220
gttctggttg ctatgtcctg tttccgccac ctctgtgaag aagcagatat tcgatgtggg      2280
gtagatgaag tgtcagtaca caacttcttg cccaactata acacattcat ggaatttgcc      2340
tcagtcagca atatgatgtc aacaggaaga gcagcgcttc agaaaagagt gatggccctg      2400
ctaaggcgca ttgagcaccc tactgcagga acattgagg cctgggaaga tacacatgca       2460
aagtgggaac aggctacaaa actaatcctt aactacccaa agccaaaat ggaagatggc       2520
caggctgcag aaaagtcttca taagaccatt gttaagagac ggatgtccca tgtcagtgga    2580
ggaggctcca tagacttgtc tgacacagac tccctgcagg agtggatcaa catgactggc      2640
ttcctttgtg cccttggtgg ggtgtgcctg caacagagaa gcagctctgg cctagcgaca      2700
tacagcccac ctatgggcgc tgtcagtgaa cgcaaagggt ctatgatttc tgtaatgtct      2760
tctgaaggga atattgattc acctgtcagc agatttatgg accggcttct gtccttaatg      2820
gtgtgtaacc acgagaaagt ggggcttcag atacggacca atgttaagga cctggtgggt      2880
ctggagttga gtcctgctct gtatccaatg ctgtttaaca aactgaagaa taccatcagc      2940
aagttttttg actctcaagg acaggtatta ctaagtgaca gcaatactca gtttgtagag      3000
caaaccatag cctaatgaa aaacctactg gataatcata ctgaaggcag ctctgagcat       3060
ctgggacaag cgagcattga acaatgatg ctaaatctgg tcagatacgt tcgtgttctt       3120
gggaatatgg tccatgcaat acaaataaaa acaaaattgt gtcagttagt tgaagtcatg      3180
atggcaagaa gagatgacct ctcgttttgt caagagatga aatttaggaa taagatggta      3240
gaatatctaa cagactgggt tatgggaaca tcaaaccaag cagcagatga tgacataaaa      3300
tgtcttcgga gagatctgga ccaagcaagc atggaagcag tagtttctct cctcgctggt      3360
cttccactgc agcccgaaga aggagatggg gtggagctga tggaggccaa atcacagtta      3420
ttccttaagt acttcacatt atttatgaac cttttgaatg actgtagtga agttgaagat      3480
gaaaatgcac aaacgggtgg caggaaacgt ggcatgtctc ggaggctggc atccctgagg      3540
cactgtacag tgcttgcaat gtcaaactta ctcaatgcta atgtggacag tggactcatg      3600
```

```
cactccatag gcttaggtta tcacaaggat cttcagacaa gagctacgtt tatggaagtt    3660
ctgacaaaaa tccttcaaca aggaacagaa ttcgatacac ttgcggaaac ggtgttggca    3720
gatcgatttg agagacttgt ggaactggtc acaatgatgg gagaccaggg agaactccct    3780
atagctatgg ctcttgccaa tgtggtccct tgttctcagt gggatgagct ggctcgggtt    3840
ctggtcactc tgtttgattc ccggcattta ctctaccagc tgctctggaa catgttttct    3900
aaggaggtag aattggcaga ctccatgcag actctctttc gaggcaacag cttggccagt    3960
aagataatga cattctgctt caaggtgtat ggtgctactt acctacaaaa gctcttggac    4020
cctttattac gagtcatcat cacatcttcg gattggcaac atgttagctt tgaagtggat    4080
cctaccaggt tagaaccctc tgagagcctt gaggagaacc agaggaacct ccttcagatg    4140
acagagaagt tcttccatgc catcatcagc tcttcctcag aattcccctc acagcttcga    4200
agtgtctgcc attgtttgta ccaggcaact tgccactccc tactgaataa agctacagta    4260
aaagaaagaa aggaaaacaa aaatcagtg gttagccagc gcttccctca gaacagcatc    4320
ggtgccgtag gaagtgccat gtttctcaga ttcatcaatc ctgccattgt ctcgccgtat    4380
gaagcaggga ttttagataa aaagccacca cctagaattg aaaggggctt gaagttaatg    4440
tcaaaggtac ttcagagcat tgccaatcat gtactgttca caaaagaaga gcatatgaga    4500 cctttaatg atttgtgaa aagcaacttt gacttggcac gaaggttttt cctagatata    4560
gcatcagatt gtcccacaag tgatgcagta aaccatagtc tttccttcat cagcgatggc    4620
aatgtgcttg ctttacatcg gctgctttgg aacaatcagg agaaaattgg ccagtatctt    4680
tccagtaaca gggatcataa agctgttgga agacgacctt ttgataagat ggccacactt    4740
ctcgcgtatc tgggtcctcc ggagcacaag cctgtggcag atacacactg gtccagcctt    4800
aaccttacca gttcaaagtt tgaggaattt atgaccaggc accaggtaca tgagaaagaa    4860
gagttcaagg ccttgaaaac gttaagcatc ttctaccaag ctggcaccctc caaagctggg    4920 aatcctattt tttattatgt tgcacggagg ttcaaaactg gccagatcaa tggtgatctg    4980
ctgatatacc atgtcttgct gactttaaag ccatattatg caaagccata tgaaattgta    5040
gtggacctta cccatactgg gcctagcaat cgctttaaaa cagacttcct ctctaagtgg    5100
tttgttgtct ttcctggctt tgcctatgac aacgtctctg cagtctatat ctataactgt    5160
aactcctggg tcagggagta taccaaatac catgagcggc tgctgactgg cctcaagggc    5220
agcaaaaggc tcattttcat cgactgtcct gggaagctgg ctgaacatat agagcatgag    5280
caacagaaac tccctgctgc taccttggct ttggaagaag atctaaaggt tttccacaat    5340
gctctcaagt tagctcacaa ggacaccaaa gtttctatta aggttggttc tactgctgtt    5400
caggtaactt cagcagaaag aacaaaagtt tggggcaat ccgtctttt aaatgatatt    5460 tactatgctt ctgaaatcga agagatctgc ctagttgatg agaaccagtt cactctaacc    5520
attgcaaacc aaggcacacc actgaccttc atgcaccaag aatgtgaagc cattgttcag    5580
tctatcattc atatcaggac ccgctgggag ctgtcacaac ctgactccat ccctcagcat    5640
accaagattc gaccaaagga tgtccctggg acactgctta atattgcgtt actgaatttg    5700
ggcagttcag accctagttt acggtctgct gcctataatc tcctgtgtgc cttaacctgc    5760
acctttaatt taaagattga aggtcagttg ctagagacat cggggttatg catccctgcc    5820
aacaacacac tcttcattgt ctctatcagt aagacgctcg cagccaatga gccacacctc    5880
accttagagt ttttggaaga gtgtatttct ggatttagca aatctagtat tgaattgaag    5940
```

```
cacctttgtt tggaatatat gaccccatgg ctgtcaaatc tagtccgttt ttgtaagcat    6000
aatgatgatg ccaaacgaca aagggttact gccatccttg ataagctaat aacaatgact    6060
ataaacgaga agcagatgta tccttctatt caagcaaaaa tctgggggag ccttgggcag    6120
atcacagacc tgctggatgt tgtgcttgac agtttcatca agaccagtgc gacaggaggc    6180
ttagggtcta tcaaagctga ggtgatggca gacacagctg tggctttagc ttctggaaat    6240
gtgaaattgg tgtcgagtaa ggttattgga aggatgtgta aaataattga caagacttgc    6300
ttatccccaa ctccaacttt agaacaacat cttatgtggg acgacattgc cattttagcc    6360
cgctacatgc tgatgctgtc cttcaacaac tccctcgatg tggcggctca tctgccctat    6420
ctcttccatg ttgtcacttt cttagtagcc acaggtccct tgtccctccg agcttccaca    6480
catgggctgc tcatcaatat cattcactct ctgtgtactt gttctcagct tcactttagt    6540
gaagagacca agcaagtttt gaggctcagt ctaacagagt tctcgttacc caaattttac    6600
ttactgtttg gcattagcaa agtcaagtcg gctgctgtca ttgccttccg ttccagttac    6660
cgggaccgct ccttctcccc tggctcctat gagagggaga cttttgcttt gacgtccctg    6720
gaaacagtca cagaagcttt gttggagatc atggaggcat gtatgagaga tattccaaca    6780
tgcaagtggc tggatcagtg gacagaacta gctcaaagat ttgcgtttca gtataaccca    6840
tcgctgcagc caagagctct tgtggtgttt ggctgtatta gcaaacgagt gtctcatggg    6900
cagataaagc agattatccg aattcttagc aaggcacttg aaagttgttt aaaaggacct    6960
gacacttaca acagtcaagt tctgatagaa tctacggtga tagcactaac aaaattacag    7020
ccgcttctta ataaggactc gcccctgcac aaagccctct tttgggttgc tgtggctgtg    7080
ctgcagctgg acgaagtcaa cttgtattca gccggcactg cacttctgga acaaaacctg    7140
cacaccttgg acagtctccg gatattcaat gacaagagtc cggaagaagt atttatggcg    7200
atccggaatc ctctggaatg gcactgcaag cagatggatc actttgtcgg actcaacttc    7260
aactctaact ttaactttgc actagttgga cacctcttaa aagggtacag gcatccttca    7320
cctgccattg ttgcaagaac agtcagaatt ttgcatacac tactaactct cgttaacaaa    7380
catagaaatt gtgacaaatt tgaggtgaat acacagagtg tggcttactt agcagctcta    7440
ctcacagtgt ctgaagaggt tcgaagtcgc tgtagcctca agcataggaa gtcccttctt    7500
cttactgata tttcaatgga aaatgttcct atggatacat atcccattca tcacggtgac    7560
cccagctata ggacactaaa ggagacccag ccatggtcct ctcccaaagg ttcagaagga    7620
taccttgcag ccacctaccc agctgtaggc caaaccagtc cccgagccag gaaatccatg    7680
agcttggata tgggacagcc ttctcaggcc aacacaaaaa aattgcttgg aacaagaaaa    7740
agttttgatc acttgatatc tgacacaaag gctcctaaaa gacaagaaat ggaatcaggg    7800
attacaacac ccccgaaaat gagaagagtg gcagagactg actatgaaat ggaaacccaa    7860
aggattccct cctcgcagca gcacccacat ttacggaaag tctcagtctc tgaatcaaat    7920
gttctttggg atgaagaagt tcttaccgac ccaaagatcc aagcgctgct tcttactgtt    7980
ctggctacac tggtaaaata tactacagat gaatttgatc aacggattct ttatgaatat    8040
ctagcagagg ccagcgttgt gtttcccaaa gtgtttcctg ttgtgcacaa tttgttggac    8100
tctaagatca ataccctctt gtctttatgc caagatccaa atttgttaaa tccaatccat    8160
ggaattgtac agagtgtggt gtaccatgag gagtccccgc cacagtacca gacatcttac    8220
ctgcaaagtt ttggttttaa tggcttatgg cggtttgcag gaccctttc aaagcaaaca    8280 caaatccctg actatgctga gctcattgtt aaatttcttg atgccttgat tgacacgtac    8340
```

```
ttgcctggaa ttgatgaaga aaccagtgag gagtccctcc tgacacccac atctccttac    8400
cctcctgcac tgcagagcca gcttagtatc actgccaacc ttaacctctc taattccatg    8460
acctcacttg caacttccca gcattcccca ggactcgaca aggagaacgt tgaactctcc    8520
cccaccgctg gccactgtaa cagtggacgg actcgccatg gatccgcaag ccaagtgcag    8580
aagcaaagaa gtgctggcag tttcaaacgt aatagcatta agaagatcgt gtgaagcgtt    8640
ctttgtttca ctcttcaaac caacctaaca tggcttctca ctagtgaccc ctcaccttgc    8700
actgctgcac ttcgtgtctt atgatcccat ctggtcgccg tgtcgccaga cggtcatctc    8760
ttggagcatt gcctaagttt aatgctgctt ttctttgatg ttttccttc tactttggca     8820
tgtgtctggt tgagcacttg ttctgaggac agcagagaca gcaggcggtc aggaggcctg    8880
actgagagcg tggaccgtgg gtgtggatga accctgcagt gctgccgctg ccgcaagcca    8940
cgggccgtac gcggaggacg gccttctgtg ttcccgtctt gcagagtgaa ggggtcgtct    9000
tagttacaca cttataagtt tgggggagaa atcatatttt aaccccagtg tatttaatct    9060
tctagctgtg gactttttt tttttttttt tttaccttat gtagttgaag gaaccacaga     9120
ggccaagcct caataaagcc acaggccagg gactgaggga ggggcaaact aatatttttgt   9180
aacgaattct taagaaatac taacatttga gtcttagcaa taagtacagg aaaataagcg    9240
tgacacacac atcttaacat tgctgaatta aagctattgg ttctgaggcc ttatacatac    9300
ttggtcatcc aacctgggta attttttttcc agttgattat cttttaattt ttacatatga   9360
aggtgttctg ttctttttt ttttttttaa gccaagacta tactaagtat agaaaactaca    9420
cttgtgtttg cacttgcttt ctcctctttc ctaagtgatt ctaagcaggg taatttgcag    9480
acagagtggt gagactcgtt tccacaaggt aattttcata gctctttcca ttggctccgt    9540
agcaaaatgg aatggtacgt gacataggt aggtgatatt tttattttgt taaataattt     9600
tccaagaaac agaatatgct gtatattatc ataaatttct ttgataagat gtatttttaa    9660
aatctttaa tcttactcct ctcctccaaa taaaatcagg aatctctagc aaaacatttg     9720
gattctatct gataggattg catttagtca ctgtgaagtc tggccggcct gtgtggtatg    9780
gacacaggac ctctaggatc gctgctgtgc agagtggctg gaccagtggg actcaggccc    9840
ttccaaggga tgcacaccca gctgcttcat ggtacccgca ggatgcaaga cagtttgact    9900
ttagtgagca cagtagtaca tggatgctct cagttaagat tgaactatat ttattttaa     9960
aaggtattat ccctctactt ccaggttccc ttcatgtatt aagacataat ggctttggga   10020
gggaccaaaa gaaacccagt agggtgtgga caggtcctgt agtgctggct cactagtgga   10080
tttcagtaag ttaaactcca cagctaagtc aataaataat ggtacattta agtattctga   10140
ctttaataat ataacacgtt tcacacttat ccatacagta acaatgtaat atgttaatgt   10200
aaataaaatt gcttttgata ttcagaaata acaatttaat ttttttaatt tgtttacagc   10260
cctgggaaaa gtaagaacca tttgccaaaa taaaaggaaa cccctagtg ttagtagtga    10320
ttttaacata gaatcactgg agactactgg agacagatgc agcaaactga gctcttgtaa   10380
aggctgcctt agaataactg tcagagcaga taaccaaggc tgggaggctg agatgccagc   10440
tgagtttagc cgcaggaggc ccgtggctta gctgccaggc ccggctcccc accgcagtac   10500
tgctggggtg cacccgctc tggctcctgc aaccgtgggc agcacagact gaggctgctg    10560
taactctagt tgcttggctt ttttaaagtc attgagttcc attactggcc cattactgtt   10620
ttgcttcccc catcaaaaca ggacaactta taaatgtgca ctcttcctgt agcgggtttc   10680
```

-continued

```
cccatagttc ttaaactgcc ccacttgagc tcctatggaa agatcaaacg gagccacttc    10740
tgaccagtac atcccaggaa actggggcag cattccagtt ttatctaata gacagaactt    10800
ccagcttttg aggaaagtct atctttgcaa gcaactgaac ctacagagct taaagtatca    10860
ctagctgccc ctcccccaaa ggagactcta attacaggag cagctgaagg tctgagtaat    10920
gtcccatttt acacaatttg gtgtgagttc tgtgattcat tttcaatttg tgtttccctg    10980
acttaaaaga aaacaaaaaa acactaacgg ctgtgtttgt gcgtttggct ggtactcctc    11040
ccctgggctc ccatgccctc actgtgggga cactgcactc tgctggacag ttactcttgc    11100
ctgcatagtg ctgaggccgg agcctggaca gtgcagactg ccacagcccc agtgggggga    11160
ctcgccccag caaccacttc cttgggggggt ttaaggttgc aagtttcctc tgggagatct    11220
ggcttttgtt ttccaggttt ggaggagttt cccccccccc cttttttttt ctacattact    11280
ccccaagcat attgaagcat gtcttattca atgttatgca atggacttcc acaaaaattc    11340
acttagtgtc agccacacaa tttttttta atgcggtata ttcccctgta aatagtttgt    11400
gtaaaatttg acagaaaagt ctatttacta cattgtaaat acatgtgatg atatattgta    11460 ttatttttgct tttttgtaaa gcagttagtt gctgtacatg gataacaaac aaaaatttga    11520
ttattcttgt gttcgtattg ttaacttctt cctgcgactg cgttccatca tttaaagaaa    11580
atgctgtgta ttgtgaactg accttgtata tgattaactt actcccctcc ccaaccaggg    11640
gttccctgcc tacaaccttg ttgataatgt aaccagcagg agaacctctg cctgacacac    11700
agactccact gctgtgggga aacatgttga cgtctgtcgc agagcatcgg cctcacttgc    11760
tcctgtcctg tgtatgccct ccctcccacc cacccccca cccacccct tttttttta    11820 aagtaaaatg taaattcaat ctgctct                                       11847
```

<210> SEQ ID NO 4
<211> LENGTH: 2841
<212> TYPE: PRT
<213> ORGANISM: Mus musculus

<400> SEQUENCE: 4

```
Met Ala Ala His Arg Pro Val Glu Trp Val Gln Ala Val Ser Arg
1               5                   10                  15

Phe Asp Glu Gln Leu Pro Ile Lys Thr Gly Gln Gln Asn Thr His Thr
                20                  25                  30

Lys Val Ser Thr Glu His Asn Lys Glu Cys Leu Ile Asn Ile Ser Lys
            35                  40                  45

Tyr Lys Phe Ser Leu Val Ile Ser Gly Leu Thr Thr Ile Leu Lys Asn
        50                  55                  60

Val Asn Asn Met Arg Ile Phe Gly Glu Ala Ala Glu Lys Asn Leu Tyr
65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
            100                 105                 110

Leu Leu Pro Glu Ile Cys His Phe Leu His Thr Cys Arg Glu Gly Asn
        115                 120                 125

Gln His Ala Ala Glu Leu Arg Asn Ser Ala Ser Gly Val Leu Phe Ser
    130                 135                 140

Leu Ser Cys Asn Asn Phe Asn Ala Val Phe Ser Arg Ile Ser Thr Arg
145                 150                 155                 160

Leu Gln Glu Leu Thr Val Cys Ser Glu Asp Asn Val Asp Val His Asp
```

-continued

```
                165                 170                 175
Ile Glu Leu Leu Gln Tyr Ile Asn Val Asp Cys Ala Lys Leu Lys Arg
            180                 185                 190

Leu Leu Lys Glu Thr Ala Phe Lys Phe Lys Ala Leu Lys Lys Val Ala
            195                 200                 205

Gln Leu Ala Val Ile Asn Ser Leu Glu Lys Ala Phe Trp Asn Trp Val
            210                 215                 220

Glu Asn Tyr Pro Asp Glu Phe Thr Lys Leu Tyr Gln Ile Pro Gln Thr
225                 230                 235                 240

Asp Met Ala Glu Cys Ala Glu Lys Leu Phe Asp Leu Val Asp Gly Phe
                245                 250                 255

Ala Glu Ser Thr Lys Arg Lys Ala Ala Val Trp Pro Leu Gln Ile Ile
            260                 265                 270

Leu Leu Ile Leu Cys Pro Glu Ile Ile Gln Asp Ile Ser Lys Asp Val
            275                 280                 285

Val Asp Glu Ser Asn Ile Asn Lys Lys Leu Phe Leu Asp Ser Leu Arg
290                 295                 300

Lys Ala Leu Ala Gly His Gly Gly Ser Arg Gln Leu Thr Glu Ser Ala
305                 310                 315                 320

Ala Ile Ala Cys Val Lys Leu Cys Lys Ala Ser Thr Tyr Ile Asn Trp
                325                 330                 335

Glu Asp Asn Ser Val Ile Phe Leu Leu Val Gln Ser Met Val Val Asp
            340                 345                 350

Leu Lys Asn Leu Leu Phe Asn Pro Ser Lys Pro Phe Ser Arg Gly Ser
            355                 360                 365

Gln Pro Ala Asp Val Asp Leu Met Ile Asp Cys Leu Val Ser Cys Phe
            370                 375                 380

Arg Ile Ser Pro His Asn Asn Gln His Phe Lys Ile Cys Leu Ala Gln
385                 390                 395                 400

Asn Ser Pro Ser Thr Phe His Tyr Val Leu Val Asn Ser Leu His Arg
                405                 410                 415

Ile Ile Thr Asn Ser Ala Leu Asp Trp Trp Pro Lys Ile Asp Ala Val
            420                 425                 430

Tyr Cys His Ser Val Glu Leu Arg Asn Met Phe Gly Glu Thr Leu His
            435                 440                 445

Lys Ala Val Gln Gly Cys Gly Ala His Pro Ala Ile Arg Met Ala Pro
            450                 455                 460

Ser Leu Thr Phe Lys Glu Lys Val Thr Ser Leu Lys Phe Lys Glu Lys
465                 470                 475                 480

Pro Thr Asp Leu Glu Thr Arg Ser Tyr Lys Cys Leu Leu Leu Ser Met
                485                 490                 495

Val Lys Leu Ile His Ala Asp Pro Lys Leu Leu Leu Cys Asn Pro Arg
            500                 505                 510

Lys Gln Gly Pro Glu Thr Gln Ser Ser Thr Ala Glu Leu Ile Thr Gly
            515                 520                 525

Leu Val Gln Leu Val Pro Gln Ser His Met Pro Glu Val Ala Gln Glu
            530                 535                 540

Ala Met Glu Ala Leu Leu Val Leu His Gln Leu Asp Ser Ile Asp Leu
545                 550                 555                 560

Trp Asn Pro Asp Ala Pro Val Glu Thr Phe Trp Glu Ile Ser Ser Gln
                565                 570                 575

Met Leu Phe Tyr Ile Cys Lys Lys Leu Thr Ser His Gln Met Leu Ser
            580                 585                 590
```

-continued

```
Ser Thr Glu Ile Leu Lys Trp Leu Arg Glu Ile Leu Ile Cys Arg Asn
        595                 600                 605

Lys Phe Leu Leu Lys Asn Lys Gln Ala Asp Arg Ser Ser Cys His Ser
610                 615                 620

Leu Tyr Leu Tyr Gly Val Gly Cys Glu Met Ser Ala Thr Gly Asn Thr
625                 630                 635                 640

Thr Gln Met Ser Val Asp His Asp Glu Phe Leu Arg Ala Cys Thr Pro
            645                 650                 655

Gly Ala Ser Leu Arg Lys Gly Arg Gly Asn Ser Ser Met Asp Ser Thr
                660                 665                 670

Ala Gly Cys Ser Gly Thr Pro Pro Ile Cys Arg Gln Ala Gln Thr Lys
            675                 680                 685

Leu Glu Val Ala Leu Tyr Met Phe Leu Trp Asn Pro Asp Thr Glu Ala
        690                 695                 700

Val Leu Val Ala Met Ser Cys Phe Arg His Leu Cys Glu Glu Ala Asp
705                 710                 715                 720

Ile Arg Cys Gly Val Asp Glu Val Ser Val His Asn Phe Leu Pro Asn
                725                 730                 735

Tyr Asn Thr Phe Met Glu Phe Ala Ser Val Ser Asn Met Met Ser Thr
            740                 745                 750

Gly Arg Ala Ala Leu Gln Lys Arg Val Met Ala Leu Leu Arg Arg Ile
        755                 760                 765

Glu His Pro Thr Ala Gly Asn Ile Glu Ala Trp Glu Asp Thr His Ala
    770                 775                 780

Lys Trp Glu Gln Ala Thr Lys Leu Ile Leu Asn Tyr Pro Lys Ala Lys
785                 790                 795                 800

Met Glu Asp Gly Gln Ala Ala Glu Ser Leu His Lys Thr Ile Val Lys
                805                 810                 815

Arg Arg Met Ser His Val Ser Gly Gly Gly Ser Ile Asp Leu Ser Asp
            820                 825                 830

Thr Asp Ser Leu Gln Glu Trp Ile Asn Met Thr Gly Phe Leu Cys Ala
        835                 840                 845

Leu Gly Gly Val Cys Leu Gln Gln Arg Ser Ser Ser Gly Leu Ala Thr
        850                 855                 860

Tyr Ser Pro Pro Met Gly Ala Val Ser Glu Arg Lys Gly Ser Met Ile
865                 870                 875                 880

Ser Val Met Ser Ser Glu Gly Asn Ile Asp Ser Pro Val Ser Arg Phe
                885                 890                 895

Met Asp Arg Leu Leu Ser Leu Met Val Cys Asn His Glu Lys Val Gly
            900                 905                 910

Leu Gln Ile Arg Thr Asn Val Lys Asp Leu Val Gly Leu Glu Leu Ser
        915                 920                 925

Pro Ala Leu Tyr Pro Met Leu Phe Asn Lys Leu Lys Asn Thr Ile Ser
930                 935                 940

Lys Phe Phe Asp Ser Gln Gly Gln Val Leu Leu Ser Asp Ser Asn Thr
945                 950                 955                 960

Gln Phe Val Glu Gln Thr Ile Ala Ile Met Lys Asn Leu Leu Asp Asn
                965                 970                 975

His Thr Glu Gly Ser Ser Glu His Leu Gly Gln Ala Ser Ile Glu Thr
            980                 985                 990

Met Met Leu Asn Leu Val Arg Tyr Val Arg Val Leu Gly Asn Met Val
        995                 1000                1005
```

His Ala Ile Gln Ile Lys Thr Lys Leu Cys Gln Leu Val Glu Val
1010                    1015                1020

Met Met Ala Arg Arg Asp Asp Leu Ser Phe Cys Gln Glu Met Lys
1025                    1030                1035

Phe Arg Asn Lys Met Val Glu Tyr Leu Thr Asp Trp Val Met Gly
1040                    1045                1050

Thr Ser Asn Gln Ala Ala Asp Asp Ile Lys Cys Leu Thr Arg
1055                    1060                1065

Asp Leu Asp Gln Ala Ser Met Glu Ala Val Val Ser Leu Leu Ala
1070                    1075                1080

Gly Leu Pro Leu Gln Pro Glu Glu Gly Asp Gly Val Glu Leu Met
1085                    1090                1095

Glu Ala Lys Ser Gln Leu Phe Leu Lys Tyr Phe Thr Leu Phe Met
1100                    1105                1110

Asn Leu Leu Asn Asp Cys Ser Glu Val Glu Asp Glu Asn Ala Gln
1115                    1120                1125

Thr Gly Gly Arg Lys Arg Gly Met Ser Arg Arg Leu Ala Ser Leu
1130                    1135                1140

Arg His Cys Thr Val Leu Ala Met Ser Asn Leu Leu Asn Ala Asn
1145                    1150                1155

Val Asp Ser Gly Leu Met His Ser Ile Gly Leu Gly Tyr His Lys
1160                    1165                1170

Asp Leu Gln Thr Arg Ala Thr Phe Met Glu Val Leu Thr Lys Ile
1175                    1180                1185

Leu Gln Gln Gly Thr Glu Phe Asp Thr Leu Ala Glu Thr Val Leu
1190                    1195                1200

Ala Asp Arg Phe Glu Arg Leu Val Glu Leu Val Thr Met Met Gly
1205                    1210                1215

Asp Gln Gly Glu Leu Pro Ile Ala Met Ala Leu Ala Asn Val Val
1220                    1225                1230

Pro Cys Ser Gln Trp Asp Glu Leu Ala Arg Val Leu Val Thr Leu
1235                    1240                1245

Phe Asp Ser Arg His Leu Leu Tyr Gln Leu Leu Trp Asn Met Phe
1250                    1255                1260

Ser Lys Glu Val Glu Leu Ala Asp Ser Met Gln Thr Leu Phe Arg
1265                    1270                1275

Gly Asn Ser Leu Ala Ser Lys Ile Met Thr Phe Cys Phe Lys Val
1280                    1285                1290

Tyr Gly Ala Thr Tyr Leu Gln Lys Leu Leu Asp Pro Leu Leu Arg
1295                    1300                1305

Val Ile Ile Thr Ser Ser Asp Trp Gln His Val Ser Phe Glu Val
1310                    1315                1320

Asp Pro Thr Arg Leu Glu Pro Ser Glu Ser Leu Glu Glu Asn Gln
1325                    1330                1335

Arg Asn Leu Leu Gln Met Thr Glu Lys Phe Phe His Ala Ile Ile
1340                    1345                1350

Ser Ser Ser Ser Glu Phe Pro Ser Gln Leu Arg Ser Val Cys His
1355                    1360                1365

Cys Leu Tyr Gln Ala Thr Cys His Ser Leu Leu Asn Lys Ala Thr
1370                    1375                1380

Val Lys Glu Arg Lys Glu Asn Lys Lys Ser Val Val Ser Gln Arg
1385                    1390                1395

Phe Pro Gln Asn Ser Ile Gly Ala Val Gly Ser Ala Met Phe Leu

-continued

```
                1400                1405                1410
Arg Phe Ile Asn Pro Ala Ile Val Ser Pro Tyr Glu Ala Gly Ile
        1415                1420                1425
Leu Asp Lys Lys Pro Pro Pro Arg Ile Glu Arg Gly Leu Lys Leu
        1430                1435                1440
Met Ser Lys Val Leu Gln Ser Ile Ala Asn His Val Leu Phe Thr
        1445                1450                1455
Lys Glu Glu His Met Arg Pro Phe Asn Asp Phe Val Lys Ser Asn
        1460                1465                1470
Phe Asp Leu Ala Arg Arg Phe Leu Asp Ile Ala Ser Asp Cys
        1475                1480                1485
Pro Thr Ser Asp Ala Val Asn His Ser Leu Ser Phe Ile Ser Asp
        1490                1495                1500
Gly Asn Val Leu Ala Leu His Arg Leu Leu Trp Asn Asn Gln Glu
        1505                1510                1515
Lys Ile Gly Gln Tyr Leu Ser Ser Asn Arg Asp His Lys Ala Val
        1520                1525                1530
Gly Arg Arg Pro Phe Asp Lys Met Ala Thr Leu Leu Ala Tyr Leu
        1535                1540                1545
Gly Pro Pro Glu His Lys Pro Val Ala Asp Thr His Trp Ser Ser
        1550                1555                1560
Leu Asn Leu Thr Ser Ser Lys Phe Glu Glu Phe Met Thr Arg His
        1565                1570                1575
Gln Val His Glu Lys Glu Glu Phe Lys Ala Leu Lys Thr Leu Ser
        1580                1585                1590
Ile Phe Tyr Gln Ala Gly Thr Ser Lys Ala Gly Asn Pro Ile Phe
        1595                1600                1605
Tyr Tyr Val Ala Arg Arg Phe Lys Thr Gly Gln Ile Asn Gly Asp
        1610                1615                1620
Leu Leu Ile Tyr His Val Leu Leu Thr Leu Lys Pro Tyr Tyr Ala
        1625                1630                1635
Lys Pro Tyr Glu Ile Val Val Asp Leu Thr His Thr Gly Pro Ser
        1640                1645                1650
Asn Arg Phe Lys Thr Asp Phe Leu Ser Lys Trp Phe Val Val Phe
        1655                1660                1665
Pro Gly Phe Ala Tyr Asp Asn Val Ser Ala Val Tyr Ile Tyr Asn
        1670                1675                1680
Cys Asn Ser Trp Val Arg Glu Tyr Thr Lys Tyr His Glu Arg Leu
        1685                1690                1695
Leu Thr Gly Leu Lys Gly Ser Lys Arg Leu Ile Phe Ile Asp Cys
        1700                1705                1710
Pro Gly Lys Leu Ala Glu His Ile Glu His Glu Gln Gln Lys Leu
        1715                1720                1725
Pro Ala Ala Thr Leu Ala Leu Glu Glu Asp Leu Lys Val Phe His
        1730                1735                1740
Asn Ala Leu Lys Leu Ala His Lys Asp Thr Lys Val Ser Ile Lys
        1745                1750                1755
Val Gly Ser Thr Ala Val Gln Val Thr Ser Ala Glu Arg Thr Lys
        1760                1765                1770
Val Leu Gly Gln Ser Val Phe Leu Asn Asp Ile Tyr Tyr Ala Ser
        1775                1780                1785
Glu Ile Glu Glu Ile Cys Leu Val Asp Glu Asn Gln Phe Thr Leu
        1790                1795                1800
```

-continued

Thr Ile Ala Asn Gln Gly Thr Pro Leu Thr Phe Met His Gln Glu
1805                    1810                1815

Cys Glu Ala Ile Val Gln Ser Ile Ile His Ile Arg Thr Arg Trp
1820                    1825                1830

Glu Leu Ser Gln Pro Asp Ser Ile Pro Gln His Thr Lys Ile Arg
1835                    1840                1845

Pro Lys Asp Val Pro Gly Thr Leu Leu Asn Ile Ala Leu Leu Asn
1850                    1855                1860

Leu Gly Ser Ser Asp Pro Ser Leu Arg Ser Ala Ala Tyr Asn Leu
1865                    1870                1875

Leu Cys Ala Leu Thr Cys Thr Phe Asn Leu Lys Ile Glu Gly Gln
1880                    1885                1890

Leu Leu Glu Thr Ser Gly Leu Cys Ile Pro Ala Asn Asn Thr Leu
1895                    1900                1905

Phe Ile Val Ser Ile Ser Lys Thr Leu Ala Ala Asn Glu Pro His
1910                    1915                1920

Leu Thr Leu Glu Phe Leu Glu Glu Cys Ile Ser Gly Phe Ser Lys
1925                    1930                1935

Ser Ser Ile Glu Leu Lys His Leu Cys Leu Glu Tyr Met Thr Pro
1940                    1945                1950

Trp Leu Ser Asn Leu Val Arg Phe Cys Lys His Asn Asp Asp Ala
1955                    1960                1965

Lys Arg Gln Arg Val Thr Ala Ile Leu Asp Lys Leu Ile Thr Met
1970                    1975                1980

Thr Ile Asn Glu Lys Gln Met Tyr Pro Ser Ile Gln Ala Lys Ile
1985                    1990                1995

Trp Gly Ser Leu Gly Gln Ile Thr Asp Leu Leu Asp Val Val Leu
2000                    2005                2010

Asp Ser Phe Ile Lys Thr Ser Ala Thr Gly Gly Leu Gly Ser Ile
2015                    2020                2025

Lys Ala Glu Val Met Ala Asp Thr Ala Val Ala Leu Ala Ser Gly
2030                    2035                2040

Asn Val Lys Leu Val Ser Ser Lys Val Ile Gly Arg Met Cys Lys
2045                    2050                2055

Ile Ile Asp Lys Thr Cys Leu Ser Pro Thr Pro Thr Leu Glu Gln
2060                    2065                2070

His Leu Met Trp Asp Asp Ile Ala Ile Leu Ala Arg Tyr Met Leu
2075                    2080                2085

Met Leu Ser Phe Asn Asn Ser Leu Asp Val Ala Ala His Leu Pro
2090                    2095                2100

Tyr Leu Phe His Val Val Thr Phe Leu Val Ala Thr Gly Pro Leu
2105                    2110                2115

Ser Leu Arg Ala Ser Thr His Gly Leu Leu Ile Asn Ile Ile His
2120                    2125                2130

Ser Leu Cys Thr Cys Ser Gln Leu His Phe Ser Glu Glu Thr Lys
2135                    2140                2145

Gln Val Leu Arg Leu Ser Leu Thr Glu Phe Ser Leu Pro Lys Phe
2150                    2155                2160

Tyr Leu Leu Phe Gly Ile Ser Lys Val Lys Ser Ala Ala Val Ile
2165                    2170                2175

Ala Phe Arg Ser Ser Tyr Arg Asp Arg Ser Phe Ser Pro Gly Ser
2180                    2185                2190

```
Tyr Glu Arg Glu Thr Phe Ala Leu Thr Ser Leu Glu Thr Val Thr
    2195                2200                2205

Glu Ala Leu Leu Glu Ile Met Glu Ala Cys Met Arg Asp Ile Pro
    2210                2215                2220

Thr Cys Lys Trp Leu Asp Gln Trp Thr Glu Leu Ala Gln Arg Phe
    2225                2230                2235

Ala Phe Gln Tyr Asn Pro Ser Leu Gln Pro Arg Ala Leu Val Val
    2240                2245                2250

Phe Gly Cys Ile Ser Lys Arg Val Ser His Gly Gln Ile Lys Gln
    2255                2260                2265

Ile Ile Arg Ile Leu Ser Lys Ala Leu Glu Ser Cys Leu Lys Gly
    2270                2275                2280

Pro Asp Thr Tyr Asn Ser Gln Val Leu Ile Glu Ser Thr Val Ile
    2285                2290                2295

Ala Leu Thr Lys Leu Gln Pro Leu Leu Asn Lys Asp Ser Pro Leu
    2300                2305                2310

His Lys Ala Leu Phe Trp Val Ala Val Ala Val Leu Gln Leu Asp
    2315                2320                2325

Glu Val Asn Leu Tyr Ser Ala Gly Thr Ala Leu Leu Glu Gln Asn
    2330                2335                2340

Leu His Thr Leu Asp Ser Leu Arg Ile Phe Asn Asp Lys Ser Pro
    2345                2350                2355

Glu Glu Val Phe Met Ala Ile Arg Asn Pro Leu Glu Trp His Cys
    2360                2365                2370

Lys Gln Met Asp His Phe Val Gly Leu Asn Phe Asn Ser Asn Phe
    2375                2380                2385

Asn Phe Ala Leu Val Gly His Leu Leu Lys Gly Tyr Arg His Pro
    2390                2395                2400

Ser Pro Ala Ile Val Ala Arg Thr Val Arg Ile Leu His Thr Leu
    2405                2410                2415

Leu Thr Leu Val Asn Lys His Arg Asn Cys Asp Lys Phe Glu Val
    2420                2425                2430

Asn Thr Gln Ser Val Ala Tyr Leu Ala Ala Leu Leu Thr Val Ser
    2435                2440                2445

Glu Glu Val Arg Ser Arg Cys Ser Leu Lys His Arg Lys Ser Leu
    2450                2455                2460

Leu Leu Thr Asp Ile Ser Met Glu Asn Val Pro Met Asp Thr Tyr
    2465                2470                2475

Pro Ile His His Gly Asp Pro Ser Tyr Arg Thr Leu Lys Glu Thr
    2480                2485                2490

Gln Pro Trp Ser Ser Pro Lys Gly Ser Glu Gly Tyr Leu Ala Ala
    2495                2500                2505

Thr Tyr Pro Ala Val Gly Gln Thr Ser Pro Arg Ala Arg Lys Ser
    2510                2515                2520

Met Ser Leu Asp Met Gly Gln Pro Ser Gln Ala Asn Thr Lys Lys
    2525                2530                2535

Leu Leu Gly Thr Arg Lys Ser Phe Asp His Leu Ile Ser Asp Thr
    2540                2545                2550

Lys Ala Pro Lys Arg Gln Glu Met Glu Ser Gly Ile Thr Thr Pro
    2555                2560                2565

Pro Lys Met Arg Arg Val Ala Glu Thr Asp Tyr Glu Met Glu Thr
    2570                2575                2580

Gln Arg Ile Pro Ser Ser Gln Gln His Pro His Leu Arg Lys Val
```

-continued

|  |  |  |  | 2585 |  |  |  | 2590 |  |  |  | 2595 |  |  |
|---|---|---|---|---|---|---|---|---|---|---|---|---|---|---|
| Ser | Val | Ser | Glu | Ser | Asn | Val | Leu | Leu | Asp | Glu | Glu | Val | Leu | Thr |
|  |  |  |  | 2600 |  |  |  | 2605 |  |  |  | 2610 |  |  |
| Asp | Pro | Lys | Ile | Gln | Ala | Leu | Leu | Leu | Thr | Val | Leu | Ala | Thr | Leu |
|  |  |  |  | 2615 |  |  |  | 2620 |  |  |  | 2625 |  |  |
| Val | Lys | Tyr | Thr | Thr | Asp | Glu | Phe | Asp | Gln | Arg | Ile | Leu | Tyr | Glu |
|  |  |  |  | 2630 |  |  |  | 2635 |  |  |  | 2640 |  |  |
| Tyr | Leu | Ala | Glu | Ala | Ser | Val | Val | Phe | Pro | Lys | Val | Phe | Pro | Val |
|  |  |  |  | 2645 |  |  |  | 2650 |  |  |  | 2655 |  |  |
| Val | His | Asn | Leu | Leu | Asp | Ser | Lys | Ile | Asn | Thr | Leu | Leu | Ser | Leu |
|  |  |  |  | 2660 |  |  |  | 2665 |  |  |  | 2670 |  |  |
| Cys | Gln | Asp | Pro | Asn | Leu | Leu | Asn | Pro | Ile | His | Gly | Ile | Val | Gln |
|  |  |  |  | 2675 |  |  |  | 2680 |  |  |  | 2685 |  |  |
| Ser | Val | Val | Tyr | His | Glu | Glu | Ser | Pro | Pro | Gln | Tyr | Gln | Thr | Ser |
|  |  |  |  | 2690 |  |  |  | 2695 |  |  |  | 2700 |  |  |
| Tyr | Leu | Gln | Ser | Phe | Gly | Phe | Asn | Gly | Leu | Trp | Arg | Phe | Ala | Gly |
|  |  |  |  | 2705 |  |  |  | 2710 |  |  |  | 2715 |  |  |
| Pro | Phe | Ser | Lys | Gln | Thr | Gln | Ile | Pro | Asp | Tyr | Ala | Glu | Leu | Ile |
|  |  |  |  | 2720 |  |  |  | 2725 |  |  |  | 2730 |  |  |
| Val | Lys | Phe | Leu | Asp | Ala | Leu | Ile | Asp | Thr | Tyr | Leu | Pro | Gly | Ile |
|  |  |  |  | 2735 |  |  |  | 2740 |  |  |  | 2745 |  |  |
| Asp | Glu | Glu | Thr | Ser | Glu | Glu | Ser | Leu | Leu | Thr | Pro | Thr | Ser | Pro |
|  |  |  |  | 2750 |  |  |  | 2755 |  |  |  | 2760 |  |  |
| Tyr | Pro | Pro | Ala | Leu | Gln | Ser | Gln | Leu | Ser | Ile | Thr | Ala | Asn | Leu |
|  |  |  |  | 2765 |  |  |  | 2770 |  |  |  | 2775 |  |  |
| Asn | Leu | Ser | Asn | Ser | Met | Thr | Ser | Leu | Ala | Thr | Ser | Gln | His | Ser |
|  |  |  |  | 2780 |  |  |  | 2785 |  |  |  | 2790 |  |  |
| Pro | Gly | Leu | Asp | Lys | Glu | Asn | Val | Glu | Leu | Ser | Pro | Thr | Ala | Gly |
|  |  |  |  | 2795 |  |  |  | 2800 |  |  |  | 2805 |  |  |
| His | Cys | Asn | Ser | Gly | Arg | Thr | Arg | His | Gly | Ser | Ala | Ser | Gln | Val |
|  |  |  |  | 2810 |  |  |  | 2815 |  |  |  | 2820 |  |  |
| Gln | Lys | Gln | Arg | Ser | Ala | Gly | Ser | Phe | Lys | Arg | Asn | Ser | Ile | Lys |
|  |  |  |  | 2825 |  |  |  | 2830 |  |  |  | 2835 |  |  |
| Lys | Ile | Val |  |  |  |  |  |  |  |  |  |  |  |  |
|  |  |  |  | 2840 |  |  |  |  |  |  |  |  |  |  |